US012678204B2

(12) United States Patent
MacAleese et al.

(10) Patent No.: US 12,678,204 B2
(45) Date of Patent: Jul. 14, 2026

(54) ROD ROCKER REDUCER INSTRUMENTS AND METHODS

(71) Applicant: MEDOS INTERNATIONAL SARL, Le Locle (CH)

(72) Inventors: Brandon MacAleese, Braintree, MA (US); Eric Biester, Barrington, RI (US); Suken Shah, Wilmington, DE (US); Firoz Miyanji, Vancouver (CA)

(73) Assignee: Medos International Sárl, Le Locle (CH)

( * ) Notice: Subject to any disclaimer, the term of this patent is extended or adjusted under 35 U.S.C. 154(b) by 221 days.

(21) Appl. No.: 18/465,108

(22) Filed: Sep. 11, 2023

(65) Prior Publication Data

US 2024/0081875 A1    Mar. 14, 2024

Related U.S. Application Data

(60) Provisional application No. 63/406,225, filed on Sep. 13, 2022.

(51) Int. Cl.
*A61B 17/70*        (2006.01)
*A61B 17/28*        (2006.01)
(52) U.S. Cl.
CPC ...... *A61B 17/7086* (2013.01); *A61B 17/2816* (2013.01); *A61B 17/282* (2013.01); *A61B 17/2833* (2013.01); *A61B 17/2841* (2013.01)
(58) Field of Classification Search
CPC .................................. A61B 17/7086–17/7089
See application file for complete search history.

(56) References Cited

U.S. PATENT DOCUMENTS

| | | | |
|---|---|---|---|
| 4,611,581 | A | 9/1986 | Steffee |
| 4,854,311 | A | 8/1989 | Steffee |
| 4,946,458 | A | 8/1990 | Harms et al. |
| 5,113,685 | A | 5/1992 | Asher et al. |
| 5,129,900 | A | 7/1992 | Asher et al. |
| 5,207,678 | A | 5/1993 | Harms et al. |
| 5,261,303 | A | 11/1993 | Strippgen |
| 5,312,404 | A | 5/1994 | Asher et al. |
| 5,443,467 | A | 8/1995 | Biedermann et al. |
| 5,476,463 | A | 12/1995 | Boachie-Adjei et al. |
| 5,522,816 | A | 6/1996 | Dinello et al. |
| 5,672,176 | A | 9/1997 | Biedermann et al. |
| 5,741,255 | A | 4/1998 | Krag et al. |

(Continued)

OTHER PUBLICATIONS

DePuy Synthes, "Matrix Spine System Surgical Technique," pp. 18 and 79, Nov. 2017.

(Continued)

*Primary Examiner* — Julianna N Harvey
(74) *Attorney, Agent, or Firm* — Barnes & Thornburg LLP

(57) ABSTRACT

Example rocker reducer instruments securely engage a receiver that is implanted in a vertebra of the spine and move a spinal fixation element, such as a rod, into a channel formed in the receiver. Example instruments pivot around their contact point with the receiver and a cross-pin or foot feature on the instrument makes contact with the spinal rod and applies a downward force to reduce the rod into the receiver. Further, example instruments can contain a stopping mechanism to limit the amount of compressing force applied to the receiver while maintaining the instrument in a rigid, closed position.

24 Claims, 30 Drawing Sheets

(56)      References Cited

U.S. PATENT DOCUMENTS

| | | | |
|---|---|---|---|
| 5,743,907 A | | 4/1998 | Asher et al. |
| 5,810,878 A | * | 9/1998 | Burel .................. A61B 17/7086 |
| | | | 606/205 |
| 6,036,692 A | | 3/2000 | Burel et al. |
| 7,722,617 B2 | | 5/2010 | Young et al. |
| 8,211,111 B2 | | 7/2012 | Dauster et al. |
| 8,216,240 B2 | | 7/2012 | Dewey |
| 8,747,409 B2 | | 6/2014 | Ichelmann et al. |
| 8,777,953 B1 | * | 7/2014 | Khalili ............... A61B 17/7086 |
| | | | 606/86 A |
| 10,058,360 B2 | | 8/2018 | Fischer et al. |
| 2007/0255284 A1 | | 11/2007 | Miller et al. |
| 2012/0203291 A1 | | 8/2012 | Boulaine |
| 2013/0190822 A1 | | 7/2013 | Rezach |
| 2013/0198022 A1 | | 8/2013 | Zhang |

OTHER PUBLICATIONS

Alhpatec "Arsenal Degenerative Spinal Fixation System Surgical Technique Guide," pp. 13 and 24, Nov. 3, 2016.
Globus "CREO AMP Modular Stabilization System Surgical Technique," pp. 15, 22, 36, Jun. 2015.
Globus Revere 6.35 "Stabilixation System Surgical Technique," pp. 2, 10, 21, 22, 35, Mar. 2010.
Metronic "CD Horizon Solera Surgical Technique," pp. 11, 31, 2011.
DePuy AcroMed "Monarch Spine System Product Catalog" 2002.
Nuvasive "Precept Technique Guide," pp. 32, 2012.
Orthopediatrics "Response Surgical Technique," pp. 14, 26, 27.
Precision Spine "Reform Pedicle Screw System Surgical Technique," pp. 25, 44, Jan. 2023.
Stryker "Serrato Surgical Technique," p. 15, Jan. 2018.
Zimmer Biomet "Polaris Deformity System Surgical Technique," pp. 11, 31, 54, 62, Aug. 2009.
Zimmer Biomet "Sequoia Surgical Technique," pp. 8, 14, Jan. 2017.
Zimmer Biomet "Vital Degenerative Surgical Technique Guide," pp. 15, 31, Jul. 2018.

* cited by examiner

ROD ROCKER REDUCER INSTRUMENTS AND METHODS

CROSS-REFERENCE TO RELATED APPLICATIONS

This application claims the benefit of U.S. Provisional Application No. 63/406,225, entitled "Rod Rocker Reducer Instruments and Methods," filed on Sep. 13, 2022. The entire contents of this application are incorporated by reference herein.

FIELD

This disclosure relates generally to surgical instruments and, more particularly, to reducer instruments utilized during spinal surgery.

BACKGROUND

During spine surgery, fixation constructs are often assembled to hold the spine in a desired shape and provide structural support to the spine. Such constructs often include a plurality of receivers (e.g., rod-receiving portions of bone screws, hooks, connectors, or the like) that are each implanted in or coupled to vertebrae of the spine, and a connecting element, such as a rod, that is received within each of the receivers and secured into the receiver using a closure such as a set screw. In such procedures, the receivers are first implanted in the vertebrae, a rod is then positioned relative to the receivers forming an interconnection between the implanted receivers, and an instrument is used to apply force to reduce the rod into each receiver. Once the rod is reduced, it must be maintained in the reduced position until a set screw is placed in the receiver to secure the rod in place. Generally, force is applied to reduce the rod into the receiver only after the receiver is implanted into a vertebra of the spine making it a delicate operation requiring significant skill and control.

The reduction of the rod into a receiver is commonly performed using tools such as pliers, levers, or in some cases, the surgeon can reduce the rod manually using their hands to create the necessary force to reduce the rod into an implanted receiver. These methods have drawbacks as they do not provide for a secure connection between the instrument and the receiver and are therefore prone to slippage and could easily damage adjacent tissue or bone. One's hands may not impart the appropriate forces required to reduce the rod and could also crowd the area preventing access to the receiver by the screw.

One instrument developed to overcome issues in spinal rod reduction is known as a rocker reducer instrument. Existing rocker reducer instruments typically have a forceps-like feature that clamps onto an implanted receiver and enables the rocker reducer instrument to pivot while securely engaged to the receiver. As the rocker reducer pivots, it makes contact with the rod and applies downward force on the rod implant to reduce the rod into a receiver. To ensure that the reducer instrument remains clamped to the implant during use, the user will have to manually maintain the clamping force or, in some cases, the instrument includes a ratcheting locking mechanism to progressively close the instrument onto the receiver. Traditional methods of securing the instrument to the receiver are not ideal as they often compress the two sides of the receiver when the instrument is closed.

Accordingly, there is a need for improved rocker reducer instruments that can securely engage with an implanted receiver and maintain the engagement in a locked position while reducing a rod into the receiver without applying excess compressing force to the receiver.

SUMMARY

Disclosed herein are rocker reducer instruments and methods of use that address the challenges of prior approaches. Example rocker reducer instruments can securely engage a receiver implanted into a vertebra of a spine, and reduce a spinal fixation element, such as a rod, into a channel formed in the receiver.

The rocker reducer instruments can be forceps-like instruments that include of a set of jaws pivotably coupled to a set of handles by a pivot mechanism or hinge. Specifically, the two handles extending from the pivot mechanism can control movement of the two jaws via the pivot mechanism, such that relative movement between the jaws corresponds to relative movement between the handles. Opposing protrusions extend from inner surfaces of the distal ends of the jaws and are aligned along the same axis when the instrument is closed. The protrusions are configured to mate with corresponding recesses on a receiver when the instrument is closed to create a secure engagement between the instrument and receiver. A cross-pin or foot feature, located proximal to the protrusions, extends perpendicular from one jaw and towards the opposing jaw, and can optionally extend into an opening in the opposing jaw.

Examples include a stopping mechanism integrated into the instrument such that when the instrument is closed around the receiver, the stopping mechanism limits the amount of clamping force applied to the receiver while the instrument is in use while still allowing the instrument to securely engage with the receiver. The stopping mechanism can be configured to prevent any clamping force from being applied to the receiver. Advantageously, the stopping mechanism can be located between the jaws or integrated with the pivot mechanism or hinge to ensure that no deflection of the jaws occurs after engagement of the stopping mechanism due to, for example, additional pressure on the handles. Generally, the locking mechanism can maintain the instrument in a rigid closed position, at least by preventing further closing of the jaws.

After the instrument is closed around the receiver, the user can apply additional force to flex the handles and engage the locking mechanism located thereon. Due to the stopping mechanism, the additional force applied to the handles to engage the locking mechanism does not result in any additional force applied to the receiver.

The stopping mechanism can be integrated into the instrument in various ways. In some embodiments, the stopping mechanism is created by a reduced diameter portion at a distal end of a cross-pin feature that extends between the jaws—extending from one jaws, where it is fixedly connected, towards and into an opening in the opposite jaw, with a step feature formed by the discontinuity where the reduced diameter portion begins configured to abut the periphery of the opening to define the closed position (e.g., the step and opening defining a stop mechanism and/or stop arrangement). Thus, in some examples, a reduced diameter portion extends into the opening on the opposed jaw when the instrument is closed around a receiver until a larger diameter portion of the cross-pin feature (disposed between the jaws) contacts the inner surface of the opposed jaw preventing further movement of the jaw relative to each other. Alternatively, or in addition, the stopping feature can be integrated into the pivot mechanism.

Once the instrument is closed onto the receiver as described above, the user can pivot the instrument about an axis defined by the contact points between the protrusions and receiver recesses. When the instrument pivots, the cross-pin or foot feature makes contact with a rod and applies a downward force to reduce and maintain the rod in the receiver. After the rod is secured in the receiver with a screw, the user can release the lock and open the instrument to release the receiver.

Any of the features or variations described herein can be applied to any particular aspect or embodiment of the present disclosure in a number of different combinations. The absence of explicit recitation of any particular combination is due solely to avoiding unnecessary length or repetition.

BRIEF DESCRIPTION OF THE DRAWINGS

The aspects and embodiments of the present disclosure can be more fully understood from the following detailed description taken in conjunction with the accompanying drawings, in which.

DETAILED DESCRIPTION

Figure 1:
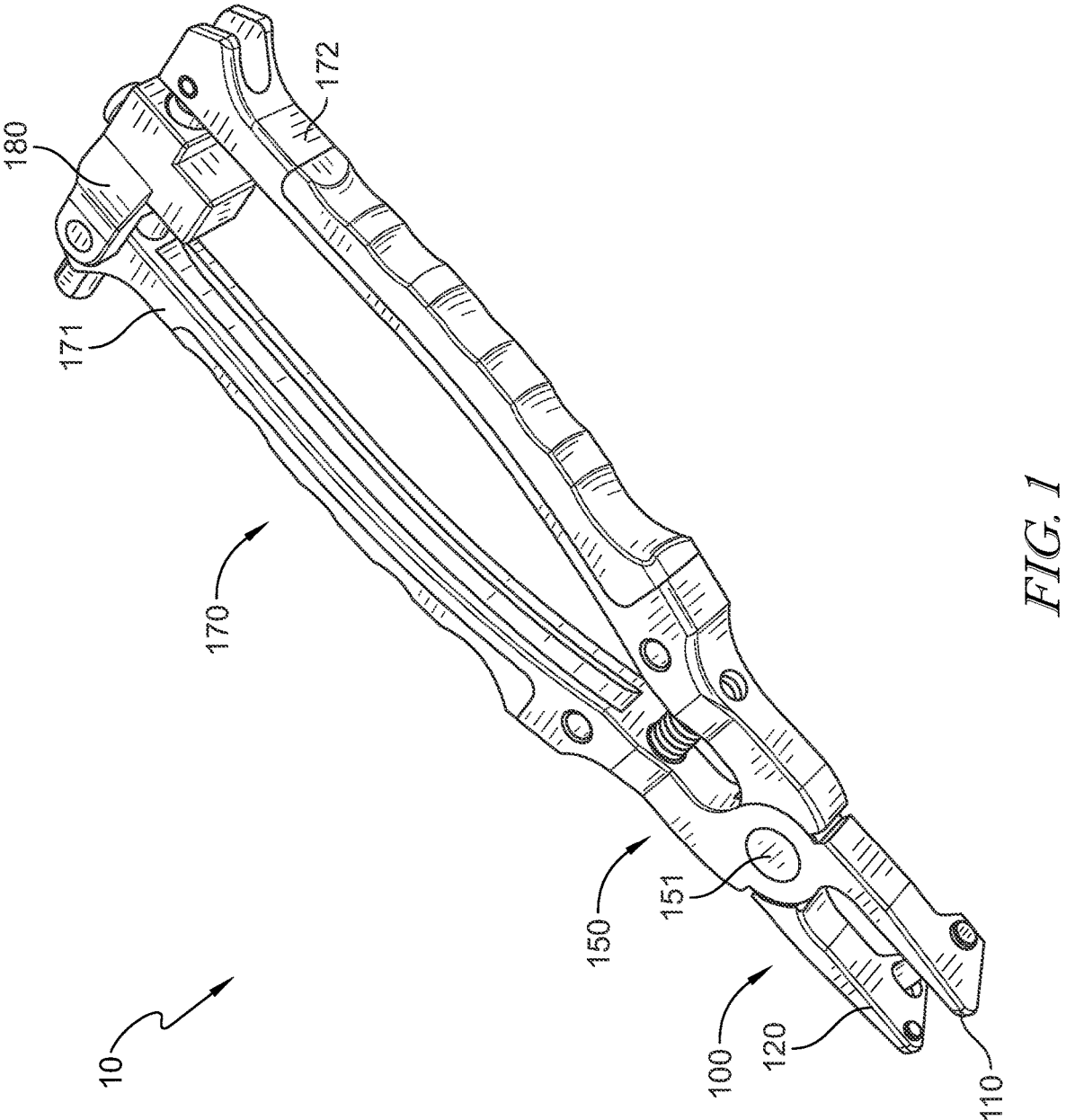
FIG. 1 is an isometric view of one example embodiment of a rod rocker reducer instrument.

Certain example embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure. Additionally, to the extent that linear, circular, or other dimensions are used in the description of the disclosed devices and methods, such dimensions are not intended to limit the types of shapes that can be used in conjunction with such devices and methods. Equivalents to such dimensions can be determined for different geometric shapes, etc. Still further, sizes and shapes of the devices, and the components thereof, can depend at least on the anatomy of the subject in which the devices will be used, the size and shape of objects with which the devices will be used, and the methods and procedures in which the devices will be used.

To the extent the present disclosure includes various terms for components and/or processes of the disclosed devices, systems, methods, and the like, such terms are merely examples of such components and/or processes, and other components, designs, processes, and/or actions are possible. In the present disclosure, like-numbered and like-lettered components of various embodiments generally have similar features when those components are of a similar nature and/or serve a similar purpose. To the extent terms such as front, back, top, bottom, proximal, distal, etc. are used to describe a location of various components of the various disclosures, such usage is by no means limiting, and is often used for convenience when describing various possible configurations.

Example rocker reducer instruments operate by engaging distal pin features with recesses on the mating implant, which enables the instrument to pivot about a single axis (e.g. the axis passing through the two recesses on the mating implant) while securely engaged to the mating implant or receiver. While the instrument is engaged, rotation of the instrument about the axis causes a cross-pin or rocker foot to apply a downward force on a rod implant to reduce the rod into a receiver. Additionally, it is advantageous to ensure that the instrument remains engaged to the receiver while the rod is reduced and examples includes a locking mechanism to lock the instrument and prevent further movement or opening of the instrument after engagement with the recesses. However, locking the instrument into a closed position while engaged with the receiver can apply an undesirable clamping force on the receiver if contact with the receiver is used to define the closed position.

Accordingly, examples of the present disclosure include stop arrangements that define a closed position in advance of clamping-contact with the receiver. Examples also include stop arrangements that are configured to allow some minimal clamping-force to be exerted onto the receiver (e.g., to ensure consistent mating between the pins and the recesses during rotation of the instrument to reduce the rod, since this can include the instrument applying a significant force onto the rod, which is reacted through the engagement between the pins and the recess.

In some embodiments, to ensure the instrument does not bottom out (e.g., compress) on the sides of a receiver, a stopping feature(s) can be integrated into the instrument that prevents the distal tips from closing together to a point where they compress with the implant. In a first embodiment (FIGS. 1-3E), a stopping feature of the instrument is on a rigid body component between the jaws, and the rigid body component also serves as the feature that applies the reduction force to the rod. In a second embodiment, (FIGS. 4A-4D) a stopping feature includes a geometric interference located at the pivot mechanism of the instrument. Additional features such as centralizing features are added in further embodiments (e.g., FIGS. 5A-5D and 9A-9H) to assist with aligning the rod as it is reduced into the receiver.

Cross Pin Rocker Instrument with Shoulder Stop

FIG. 1 is an isometric view of one example embodiment of a rod rocker reducer instrument 10 according to the present disclosure. The instrument 10 is configured to reduce a spinal rod into a receiver implanted in a vertebra of the spine. The instrument 10 includes opposing jaws 100 pivotably connected by an adjustment mechanism 150 and a proximal handle 170 s control movement of the opposing jaws 100 (e.g., opening and closing) by respecting opening and closing of first and second handle arms 171, 172 of the proximal handle 170. The opposing jaws 100 includes a first jaw 110 coupled to a first handle arm 171 and a second jaw 120 coupled to a second handle arm 172. The arms 171, 172 of the proximal handle 170 extends from the adjustment mechanism 150 and control movement of the jaws. One or more parts of the instrument 10 can be made from a hard material, such as metal or plastic, which allows a force on the proximal handle 170 to deliver to force to the distal end of the jaws 100.

As explained in more detail below, the instrument 10 operates by capturing spinal fixation elements, such as a receiver and a rod, between the first jaw 110 and the opposing second jaw 120. Once the receiver and rod are captured in the jaws 100, the instrument 10 can reduce or translate a rod into a rod-receiving portion of the receiver. To capture the receiver between the jaws 100, a user can move the instrument from an open position to a closed position by moving the first handle 171 toward the second handle 172 causing the first jaw 110 and second jaw 120 to move toward each other via the adjustment mechanism. As shown in FIG. 1-2F, the adjustment mechanism 150 includes a pivot arrangement 151 coupled to the proximal end of the first jaw 110 and the proximal end of the second jaw 120 such that the first jaw 110 and second jaw 120 rotate between the open position and closed position when the first handle 171 is moved toward the second handle 172. A locking mechanism 180 is disposed between the proximal ends of the first handle 171 and second handle 172 to selectively lock the instrument 10 in the closed position.

Figures 2A, 2B, 2C:
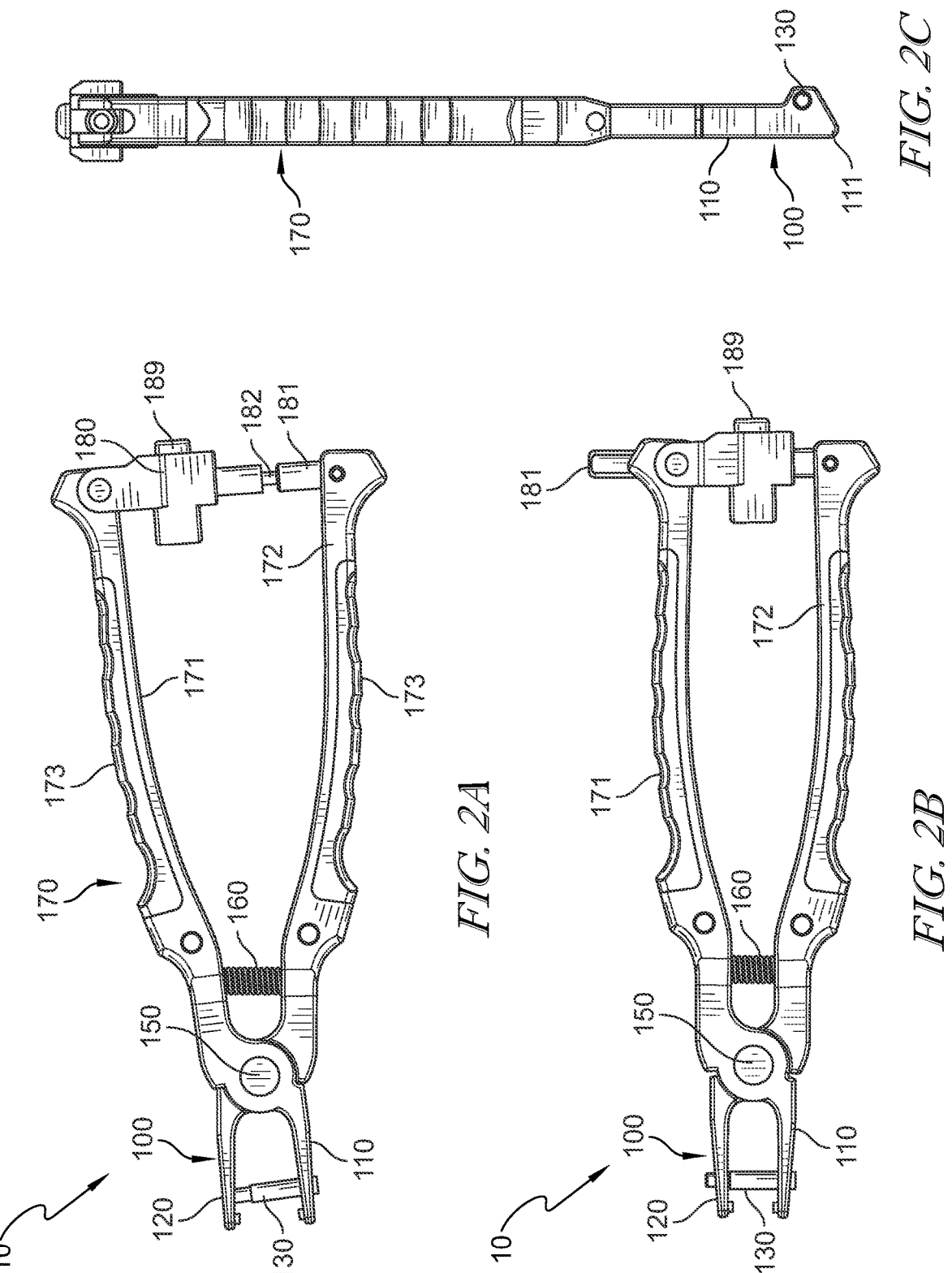
FIG. 2A is a top view of the instrument of FIG. 1 in an open position.
FIG. 2B is a top view of the instrument of FIG. 1 in a closed position.
FIG. 2C is a side view of the instrument of FIG. 1.

FIG. 2A is a top view of the instrument 10 in an open position. Each arm 171, 172 of the proximal handles 170 of the instrument 10 can include a grip surface 173 to facilitate user grasping. For example, the grip surface 173 can be ridged to seat a user's fingers or additional features to assist in comfort and ease of use. The first jaw 110 includes a rigid body 130 extending from the first jaw 110 towards the second jaw 120. The rigid body 130 is configured to contact a rod and apply a force to the rod as the instrument 10 is pivoted about the distal end of the jaws 100. The rigid body 130 is illustrated as having a cylindrical outer shaper, but those skilled in the art will appreciate that a number of different shapes are possible for engagement with a rod in a perpendicular orientation, such a as a rigid body having a rounded face that engages against the rod.

Figures 2D, 2E:
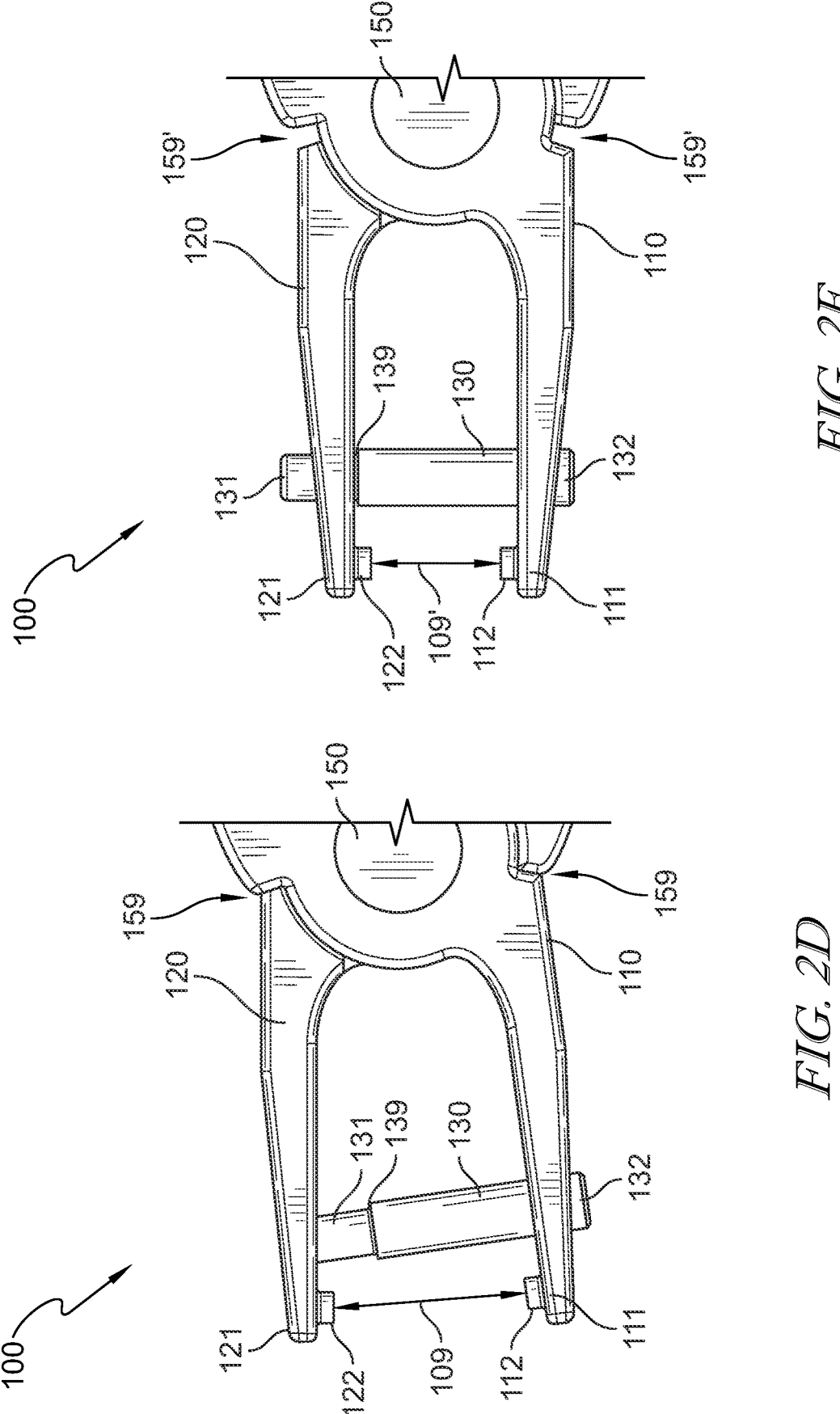
FIG. 2D is a top detail view of jaws of the instrument of FIG. 1 in an open position.
FIG. 2E is a top detail view of jaws of the instrument of FIG. 1 in a closed position.
Figure 2F:
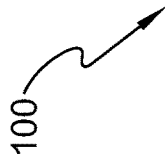
FIG. 2F is an isometric detail view of jaws of the instrument of FIG. 1 in an open position.

When the instrument 10 is in the open position (as shown in FIGS. 2A and 2D), the first handle arm 171 and the second handle arm 172 are maximally spaced apart and therefore the first jaw 110 and second jaw 120 are maximally spaced apart. The instrument 10 can contain a biasing mechanism 160 to bias the instrument 10 towards the open position. The biasing mechanism 160 can be a spring located between the first handle arm 171 and second handle arm 172 proximal to the adjustment mechanism 150. A number of different biasing mechanisms and arrangements exist for use with plier-like or forceps-like devices.

The locking mechanism 180 is configured to remain unlocked while the instrument is in the open position. The locking mechanism 180 can include a sliding bar 181 with a notch 182 that moves into engagement with a selective retention mechanism (e.g., a locking pin or spring plunger) of the locking mechanism 180 as the first handle arm 171 and second handle arm 172 move towards each other (e.g., to close the jaws 100). The selective retention mechanism within the locking mechanism 180, when engaged with the notch 182, fixes the position of the sliding bar 181 to fix the handle arms 171, 172 relative to one another. The single notch 182 defines a singular locking position of the handle arms 171, 172, corresponding to the engagement of the single notch 182 with the selective retention mechanism.

When the instrument 10 is in the closed position as illustrated in FIG. 2B, the first jaw 110 and second jaw 120 are minimally spaced apart. In some examples, the locking mechanism 180 is configured to remain unlocked when the first jaw 110 and second jaw 120 are in the closed position. Once the instrument 10 is closed, a user can apply a squeezing pressure to flex the handle arms 171, 172 further together to engage the locking mechanism 180, as described above. In other examples, the locking mechanism 180 is configured to capture and hold the jaws 100 in the closed position as soon as the closed position is reached. Because the locking mechanism 180 can define a retained position of the handles 170 and jaws 100 (e.g., closed), advantageously the instrument can include a stop arrangement, described in more detail below, within the jaws 100 or adjustment mechanism 150 that structurally defines the closed position at the location of the stop arrangement (e.g., and not at the location of the locking mechanism 180, which can be at the proximal end of the handles 170). Accordingly, engagement of the locking mechanism 180 after engagement of the stop arrangement (e.g., by arranging the locking mechanism 180 to only engage after flexure of the handles 170 after engagement of the stop arrangement) can ensure that the stop arrangement defines the closed position of the jaws 100 and that the engagement of the locking mechanism 180 maintains the instrument in the closed position without any play or slop between jaws 100. The locking mechanism 180 can contain a release mechanism 189 to release the selective retention mechanism after operation of the instrument 10. In the present embodiment the release mechanism 189 is illustrated as a button that can be pressed, after the locking mechanism 180 has engaged the notch 182, to release the sliding bar 181 and allow the handle arms 171, 172 and jaws 100 to be opened.

A side view of the instrument 10 is illustrated in FIG. 2C. In this view, the distal end 111 of the first jaw 110 is shown. The distal end 111 is configured to grasp a receiver to initiate a rod reduction operation, which is shown in more details in FIGS. 2D and 2E.

FIGS. 2D and 2E illustrate detailed views of jaws 100 of the instrument 10. A first protrusion 112 is located on the distal end 111 of the first jaw 110 and a second protrusion 122 is located on the distal end 121 of the second jaw 120. The first protrusion 112 and second protrusion 122 are arranged to contact opposing sides of a spinal implant in the closed position. While the first and second protrusions 112, 122 are illustrated as cylindrical sections, a number of different engagement geometries are possible such that engagement features (e.g., protrusions) on each jaw can engage with complimentary engagement features on opposite sides of receiver to enable single-axis rotation of the jaws of the instrument 10 about the complimentary engagement features. When the jaws 100 of the instrument 10 are in the open position, as shown in FIG. 2D, the first protrusion 112 and second protrusion 122 are spaced apart at a maximum distance 109. Surfaces on the adjustment mechanism 150 can make contact points 159 with the proximal end of the first jaw 110 and the proximal end of the second jaw 120 to define the maximum open distance 109. In the closed position, shown in FIG. 2E, the first protrusion and second protrusion are spaced apart at a minimum distance 109'. In the closed position, the first protrusion 112 and the second protrusion 122 extend towards each other along the same axis, which enables single axis rotation of the instrument 10 when the protrusions 112, 122 are disposed in complimentary recesses (e.g., cylindrical recesses disposed on opposite sides of a receiver and extending along a common axis). The surfaces 195 on the adjustment mechanism mentioned above are not in contact with the proximal ends of the jaw 100 when the instrument is closed creating a gap 159'.

As shown in more detail in FIG. 2F, the rigid body 130 is configured to extend from the first jaw 110 into an opening 129 in the second jaw 120. The opening 129 is appropriately sized to allow a length (e.g., a reduced diameter portion 131) of the rigid body to move freely in the opening 129 when the instrument 10 moves from an open position to a closed position. The rigid body 130 of the first jaw is offset from a proximal-distal axis of the first jaw with respect to the first distal protrusion 111 (as shown more clearly in FIG. 2C). Similarly, the opening 129 is offset from a proximal-distal axis of the second jaw 120 with respect to the second distal protrusion 121 to correspond with the location of the rigid body 130. When the jaws 100 of the instrument 10 capture a receiver, the first distal protrusion 111 and second distal protrusion 122 can be disposed within recesses located on opposing sides of the receiver, thereby permitting the distal ends 111, 121 of the jaws 100 to pivot about the spinal implant and reduce a rod via engagement by the rigid body 130.

The instrument 10 also includes a stop arrangement to define the closed position of the jaws 100, such that, in the closed position, the first protrusion 112 and the second protrusion 122 are spaced apart 109' more than the width of the receiver. This prevents the jaws 100 from exerting a clamping force on the receiver when the instrument 10 is in operation. In the embodiment shown in FIGS. 2D and 2E, the stop arrangement includes a transition region 139 (e.g., an axial-facing facing step) defined by a sharp transition where the reduced diameter portion 131 of the rigid body 130 begins. In the closed position, shown in FIG. 2E, the reduced diameter portion 131 is disposed in the opening of the second jaw 120 and the transition region 139 contacts the inner surface of the second jaw 120 and thereby geometrically prevents further closure of the jaws 100 and therefore the protrusions.

Figure 3A:
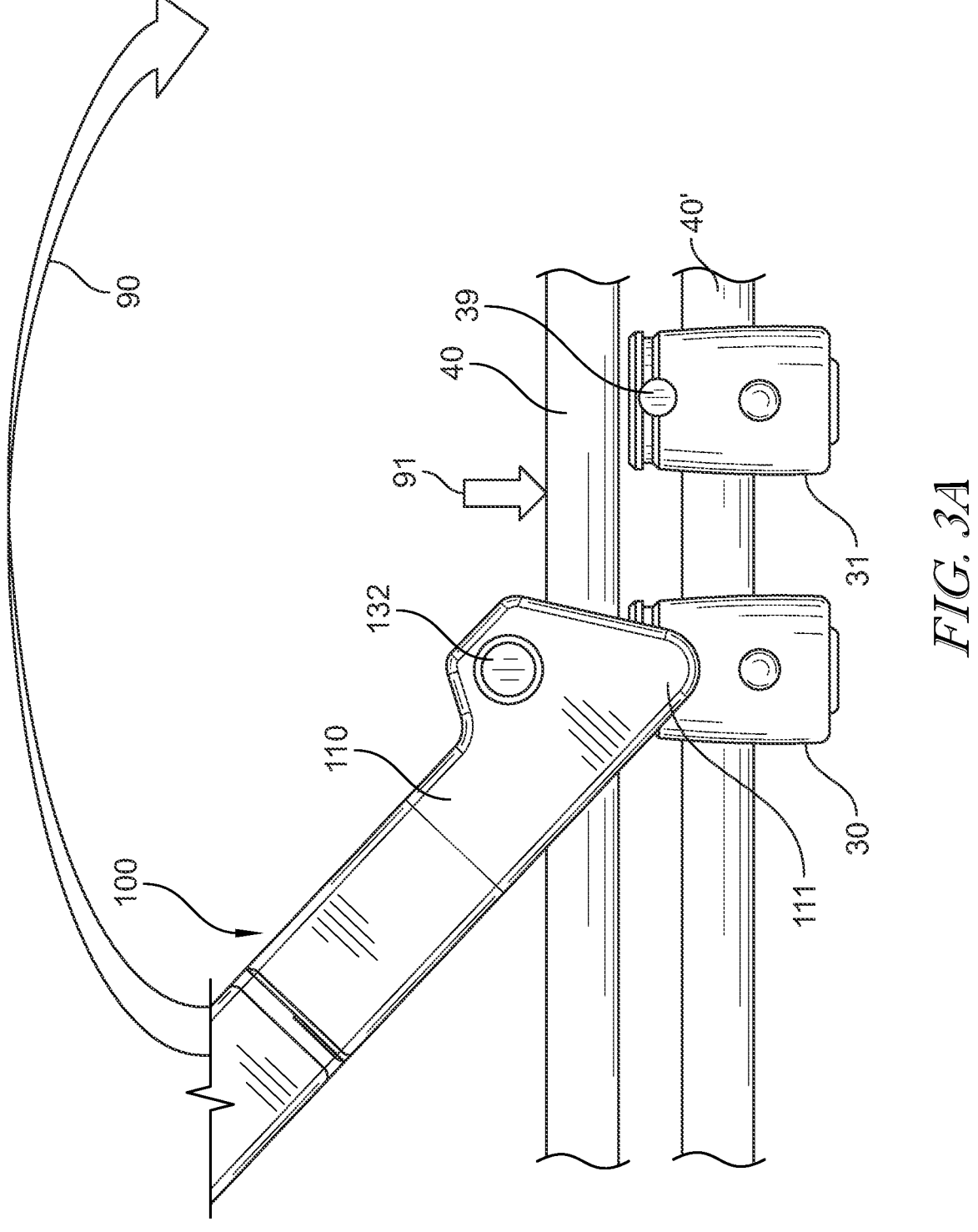
FIG. 3A is a side view of the instrument of FIG. 1 coupled with a rod receiver and conducting a rod reducing operation in an initial position before reducing the rod into the receiver.

FIGS. 3A-3E illustrate a rod-reducing operation using the instrument 10 of FIGS. 1-2E. FIG. 3A is a side view of the instrument 10 coupled with a receiver 30 and conducting a rod reducing operation in an initial position before reducing the rod 40 into the receiver 30. While the illustrated receiver is a head of a polyaxial pedicle screw, it will be appreciated that the instrument 10 can be used with other receivers instead or in addition, such as other types of screws, hooks, connectors, and the like. As discussed above, the instrument 10 operates by capturing spinal fixation devices, such as a receiver 30 and a rod 40 within the jaws 100 and pivots to move the rigid body 130 against the rod to reduce the rod 40 into the receiver 30. When the instrument 10 and receiver 30 are coupled in the initial position shown in FIG. 3A, the first protrusion 112 and second protrusion 122 are disposed in instrument-receiving recesses 39 of the receiver 30 by disposing the jaws 100 around the receiver 30 in the open position and squeezing the handles 170 to close the jaws 100 towards the sides of the receiver 30, which disposes the protrusions 112, 122 in respective opposing recesses 39 without applying a clamping force on the receiver 30 (e.g., because engagement of the stop arrangement is triggered before or immediately coincident with contact of the jaws 100 with the receiver that prevents further closure of the jaws). The opposing recesses 39 are located at opposing sides of the receiver 30 and can be any position along the length of the receiver, and preferably equally opposite both sides of a rod-receiving recess of the receiver 30 (e.g., to enable symmetrical pivoting movement of the instrument to reduce the rod 40). In the present embodiment, the recesses 39 are circular indents, but can take on a variety of shapes and sizes to optimize a secure fit with the protrusions.

Figure 3B:
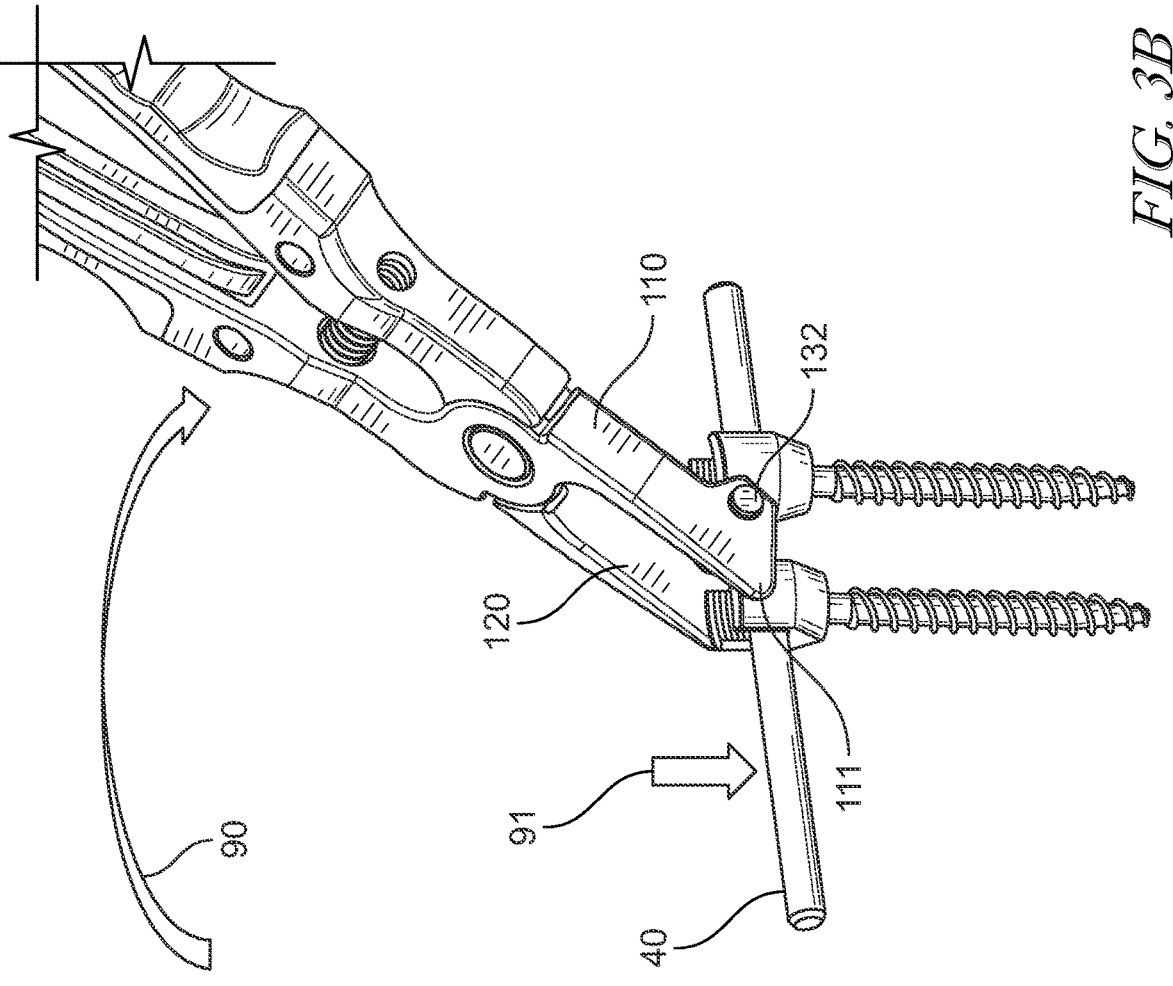
FIG. 3B is an isometric view of the instrument of FIG. 3A coupled with a rod receiver and conducting a rod reducing operation in a final position after reducing the rod into the receiver.

In the initial position of FIG. 3A, the rod 40 is positioned above a rod-receiving recess of the receiver 30 and the rigid body 130 is positioned above and perpendicular to the rod 40. A user reduces the rod 40 into the receiver 30, by rotating the instrument 10 about the contact points between the distal protrusions 112, 122 and recesses 39. The direction of rotational movement of the jaws 100 is shown as arrow 90 in FIG. 3A. As the instrument 10 is rotated, the rigid body 130 makes contact with the rod 40 and translates/urges the rod 40 in a downward direction 91 (e.g., toward the receiver 30) until the rod 40 reaches a final position (as indicated by shaded rod 40') seated within the receiver 30. The final position 40' of the rod 40 is illustrated in FIG. 3B, which shows the instrument 10 coupled with the receiver 30 and rotated fully such that the rod 40 is reduced while the receiver remains captured by the first jaw 110 and the second jaw 120.

Figure 3D:
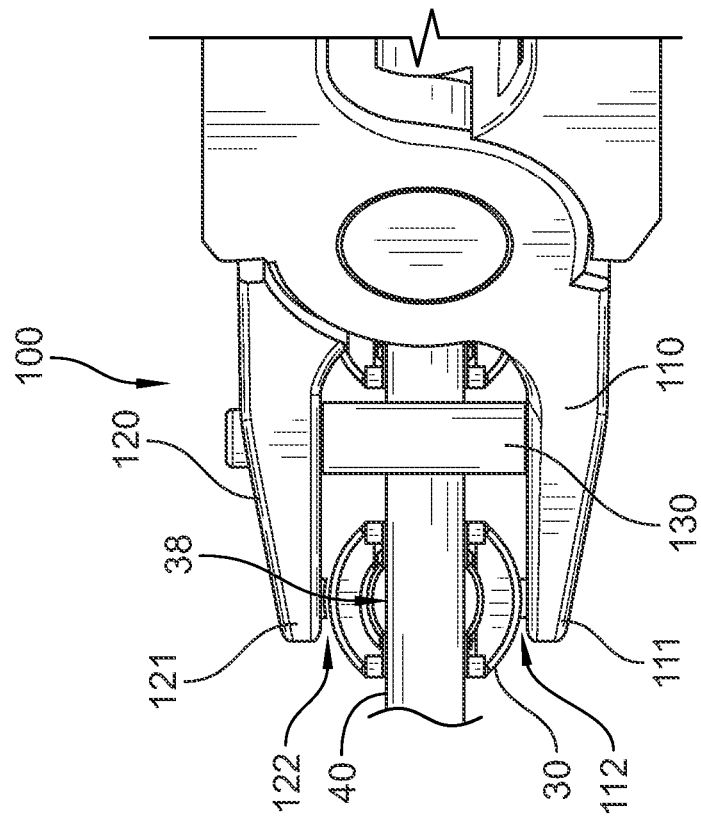
FIG. 3D is a top detail view of the jaws of the instrument of FIG. 3A in the final position.
Figure 3C:
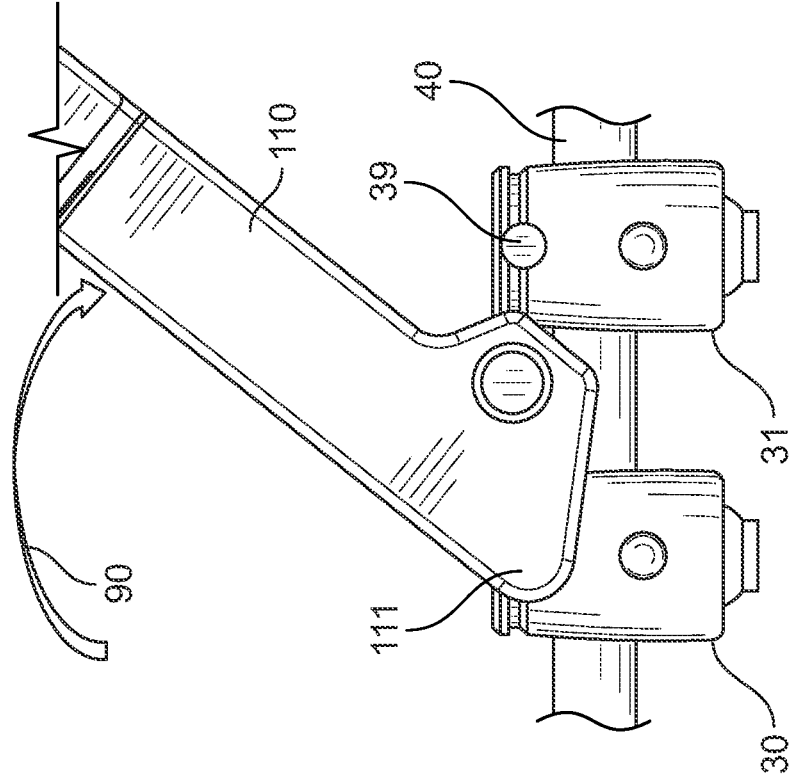
FIG. 3C is a side detail view of the jaws of the instrument of FIG. 3A in the final position.

FIG. 3C shows a detailed side view of the jaws 100 coupled to a receiver 30 and the rod 40' reduced to a final position. The rod 40 is reduced fully into a rod-receiving recess of the receiver 30. In FIG. 3D, a top view of the rod 40 reduced into the receiver 30 is shown. From above, the first protrusion 111 and second protrusion 121 are shown disposed in opposing recesses on the receiver 30 allowing the jaws 100 to capture the receiver as the rigid body 130 makes contact with the rod 40'.

Figure 3E:
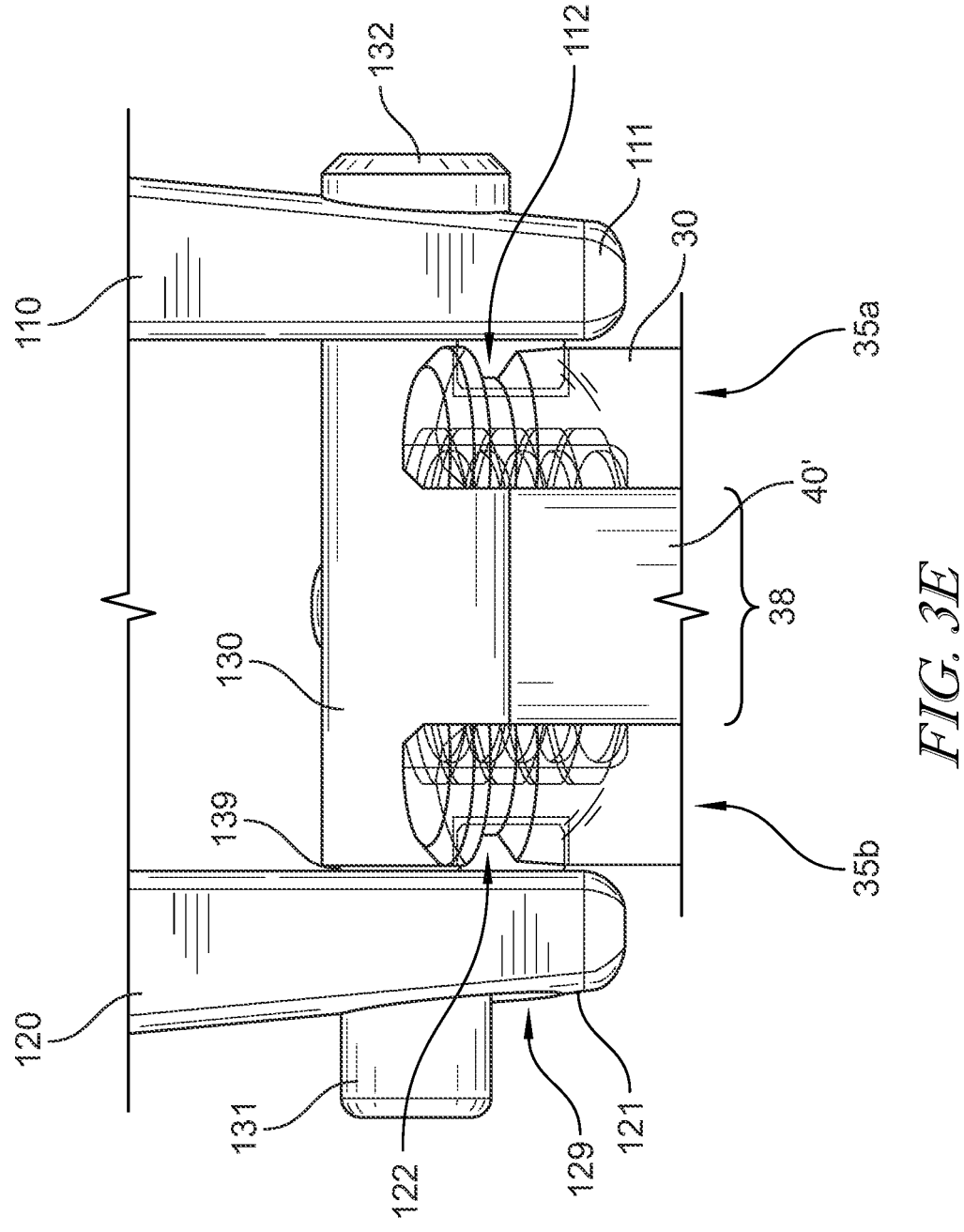
FIG. 3E is a front detail view of the jaws of the instrument of FIG. 3A in the final position.

A more detailed view of the rod 40' in the final position is shown in FIG. 3E. A rod-receiving recess 38 is defined by the first arm 35a and the second arm 35b of the receiver 30. The function of the stop arrangement (e.g., the transition region 139 of the rigid body 130 is in contact with the second jaw 120 to prevent further movement between the first distal protrusion 111 and the second distal protrusion 122) is more clearly illustrated in FIG. 3E, with the first distal protrusion 111 disposed in a recess on the first wall 35a of the receiver and the second distal protrusion 122 is disposed in the second wall of the receiver 35b without inner surfaces of the first jaw 110 and second jaw 120 contacting the receiver 30 (and without the protrusions 112, 122 bottoming out in the recesses 39).

Cross Pin Rocker Instrument with Hinge Joint Stop

Figures 4A, 4B, 4C:
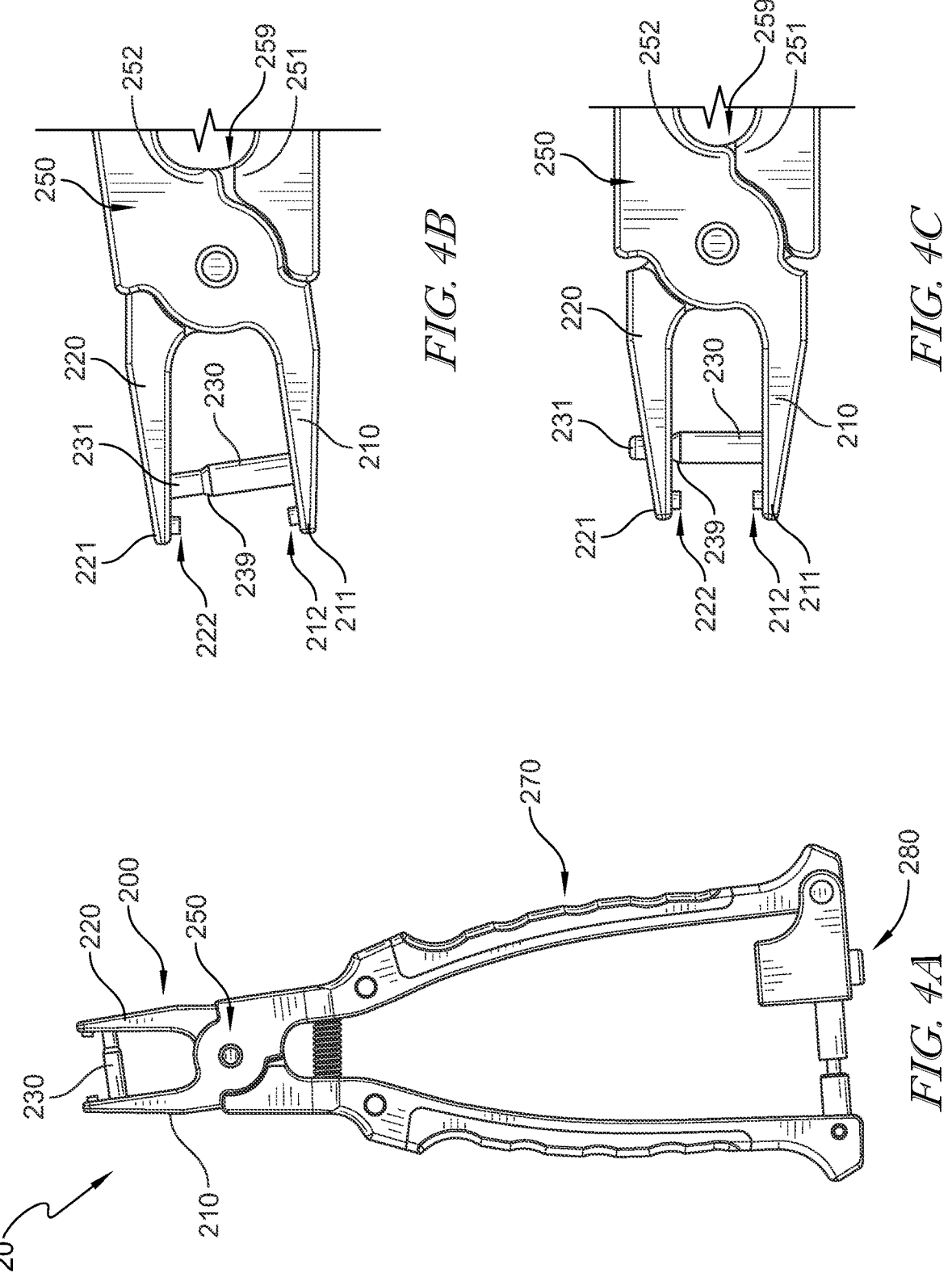
FIG. 4A is a top view of another example embodiment of a rod rocker reducer instrument in an open position.
FIG. 4B is a top detail view of the jaws of the instrument of FIG. 4A in the open position.
FIG. 4C is a top detail view of the jaws of the instrument of FIG. 4A in a closed position.

FIGS. 4A-4D illustrate an alternative embodiment of an instrument 20 according to the present disclosure. Similar to the embodiment described above, the present embodiment includes a first jaw 210 and a second jaw 220 that are coupled to a pair of handles 270 by an adjustment mechanism 250 and a locking mechanism 280 can be disposed between the proximal ends of the handles 270 as shown in FIG. 4A. The present embodiment differs from the embodiment described above in that the stopping mechanism is located on the adjustment mechanism. In the present embodiment, the stop arrangement is defined by a geometric interference between a first surface 251 and a second surface 252 on the adjustment mechanism 250. FIG. 4B is a top detailed view of the jaws 200 in the open position. When the instrument 20 is open, there is a gap 259 between the first surface 251 and the second surface 252 of the adjustment mechanism 250. When the instrument 20 closes, as shown in FIG. 4C, the first surface 251 contacts the second surface 252 creating a geometric interference. This contact point 259' prevents further movement of the first jaw 210 towards the second jaw 220.

Figure 4D:
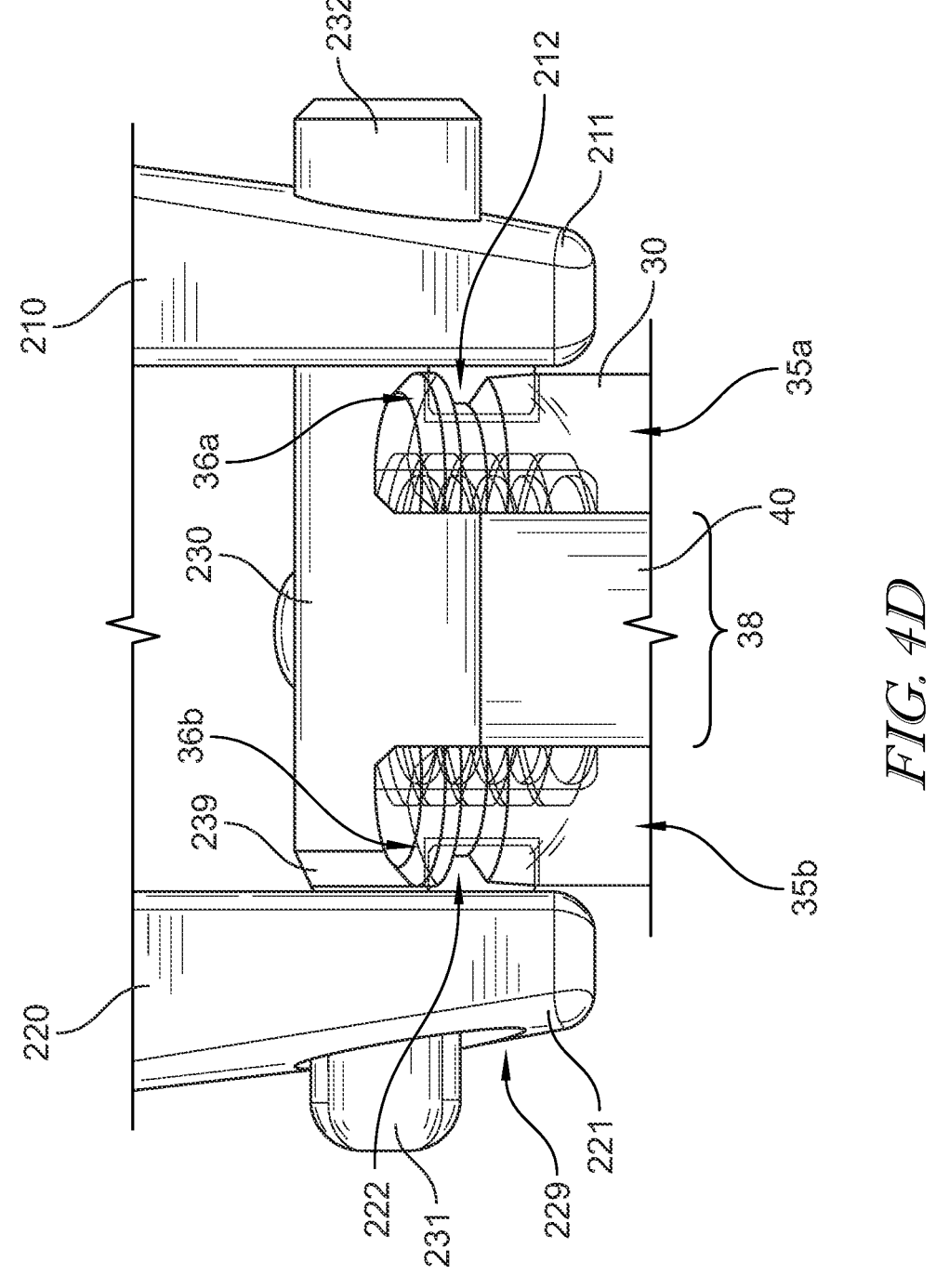
FIG. 4D is a front detail view of the jaws of the instrument of FIG. 4A in a closed position coupled with a receiver and in a final position after conducting a rod reducing operation to dispose a rod in the receiver.

FIG. 4D shows a front detail view of the jaws of the instrument 20 in a closed position coupled with a receiver 30 and in a final position after conducting a rod reducing operation to dispose a rod 40' in the receiver. In the example embodiment, a first protrusion 212 extends from a distal end 211 of the first jaw 210 and a second protrusion 222 extends from a distal end 221 of a second jaw 220. Similar to the embodiment above the first and second protrusions 212, 222 extend towards each other along the same axis when the instrument 20 is closed. A user can couple the instrument 20 with a receiver 30 by aligning the distal ends of the first and second jaws 221, 221 on opposing sides of the receiver 30 and inserting the first and second protrusions 212, 222 into corresponding recesses 36a, 36b located on first and second side walls 35a, 35b of the receiver 30. When the instrument is in use, the first and second protrusions 212, 222 remain disposed with the recesses 36a, 36b and the contact point between the first and second protrusions 212, 222 and recesses 36a, 36b serves as a point of rotation for the instrument 20.

In the present embodiment, the rigid body 230 extends from the first jaw 210 towards the second jaw 220 and comprises a cylinder section with a reduced diameter portion 231 at the distal end that begins with a sloped transition portion 239. When the instrument 20 is closed, the reduced diameter portion 231 is disposed within an opening 229 on the left jaw 221. Similar to the embodiment described above, the opening 229 is appropriately sized to allow the reduced diameter portion 231 to move freely within the opening when the instrument 20 is move from an open position to a closed position. As illustrated, the rigid body 230 is configured to contact a rod 40 and reduce the rod 40 to a final position within a rod-receiving recess 38 of a receiver 30. The rod-receiving recess 38 is formed in the space in the receiver 30 between a first arm 35a and a second arm 35b.

Cross Pin Rocker Instrument with Shoulder Stop and Centralizing Features

FIGS. 5A-5D illustrate an additional embodiment of the jaw 300, which contains a centralizing feature for aligning a rod 40 prior to rotation of the instrument to reduce the rod into the recess of a receiver. In operation, the centralizing feature(s) ensure that the rod is positioned above the rod-receiving recess. A top view of the jaws 300 is shown in the open position in FIG. 5A and the closed position in FIG. 5B. In the example embodiment of the jaws 300, a first centralizing feature 315 is formed on or fixed to the distal end 311 of the first jaw 310 and a second centralizing feature 325 is formed on or fixed to the distal end 321 of the second jaw 320. Similar to the distal protrusions 312, 322. The centralizing features 315, 325 extend medially towards each other on the same axis when the jaw 300 are closed.

Figures 5A, 5B:
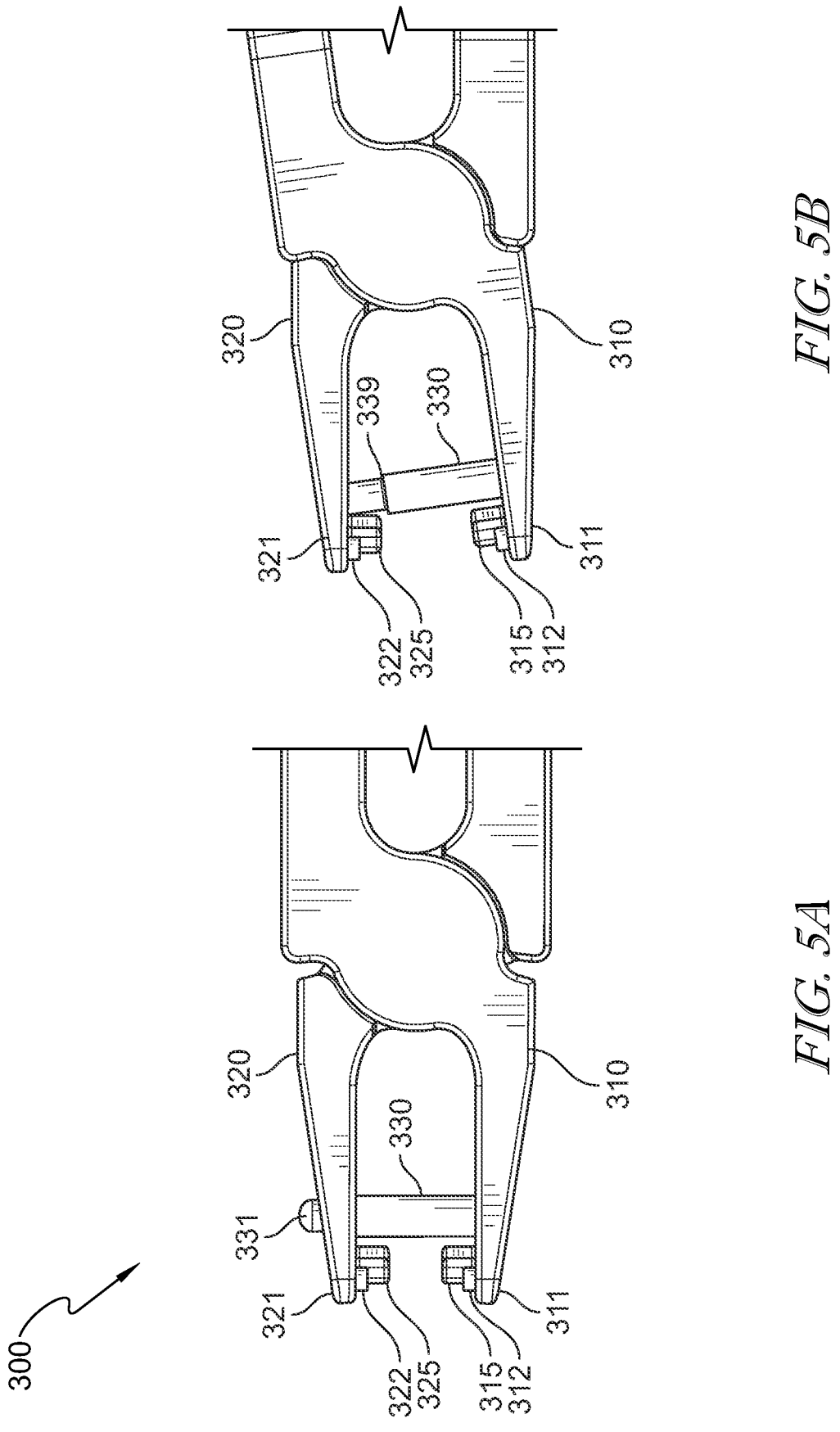
FIG. 5A is a top detail view of the jaws and pivot mechanism of yet another example embodiment of a rod rocker reducer instrument in a closed position.
FIG. 5B is a top detail view of the jaws and pivot mechanism of the instrument of FIG. 5A in an open position.
Figures 5C, 5D:
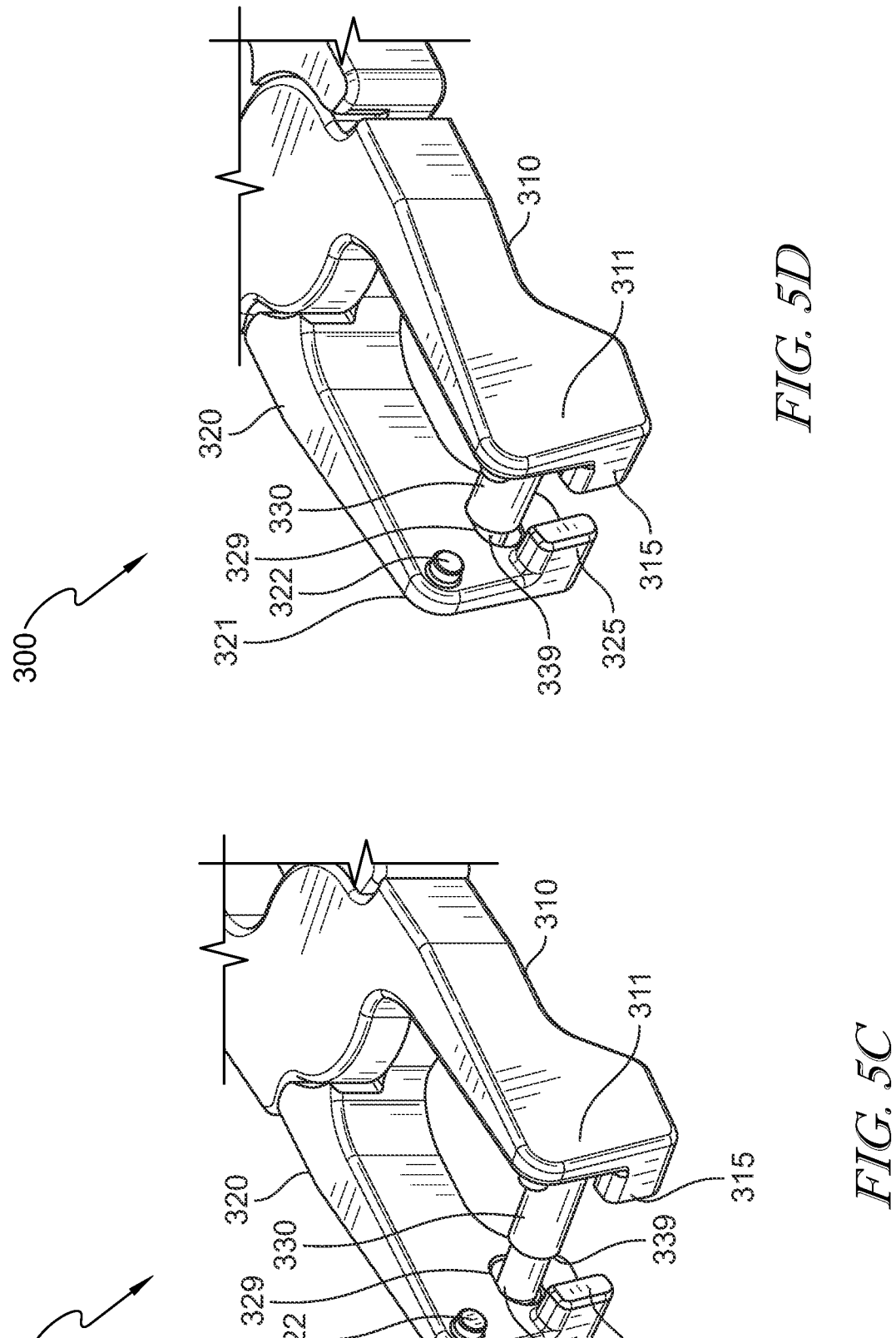
FIG. 5C is an isometric view of the of the jaws of the instrument of FIG. 5A in an open position.
FIG. 5D is an isometric view of the of the jaws of the instrument of FIG. 5A in a closed position.

FIGS. 5C and 5D show the centralizing features 315, 325 of the jaw from the side. The first centralizing feature 315 and second centralizing feature 325 are located towards the bottom of the jaws 300 with respect to the first and second distal protrusions 312, 322. In the closed position, shown in FIG. 5D, the centralizing features 315, 325 are spaced and arranged to contact a spinal rod and align it within a rod-receiving recess of the receiver. The centralizing features are shown here as rectangular protrusions but they can take on a variety of shapes and sizes to best suit the type and size of spinal rod used. When the instrument is in use, the jaws 300 are closed around a receiver with a rod disposed therein. As the first jaw 310 and second jaw 320 move together to close the instrument, the first centralizing feature 315 makes contact with a side of the rod and a second centralizing feature 325 makes contact with the opposing side of the rod and moves the rod to a predefined position aligned with the rod-receiving recess of the receiver.

The centralizing features 315, 325 located in the position shown in FIGS. 5C and 5D have a benefit of allowing access to insert a set screw into the receiver because the centralizing features 315, 325 do not occlude the top of the receiver 30 when the rocker instrument has fully reduced the rod. In contrast, as shown in the instrument embodiment of FIG. 9H, a centralizing feature 715 may be positioned above the axis of the receiver 30 in certain orientations of the instrument.

FIGS. 5A-5D also illustrate additional details regarding the cross pin 330 disposed between the jaws 310, 320. The cross pin 330 extends from an inner-facing surface of the distal end 311 of the first jaw 310 towards the distal end 321 of the second jaw 320. The end of the cross pin is formed as a reduced diameter section 331 formed beyond a step 339. The reduced diameter section 339 is disposed within an opening 329 within the distal end 321 of the second jaw 320, with the opening being sized and shaped to enable the reduced diameter section 331 to move within the opening 329 as the jaws 310, 320 open and close without permitting the cross pin 330 to enter the opening 329 beyond the step 339. Accordingly, the step 339, in the closed position of the jaws 310, 320 as shown in FIGS. 5A and 5D, contacts the inner surface of the distal end 321 of the second jaw 320 and thereby defines the closed position of the jaws 310, 320 such that no further closure is possible due to the inability of the cross pin 330 to enter any further into the opening 329.

Footed Rocker Instrument with Distal End Stop

FIGS. 6A-6D illustrate an alternative embodiment of the jaws 400 where the rigid body 440 includes a third protrusion 441 extending downward from the rigid body and configured to the contact a spinal rod and reduce the rod into a receiver. The third protrusion 441 can be a foot, nub, or other type of rigid extension.

Figure 6B:
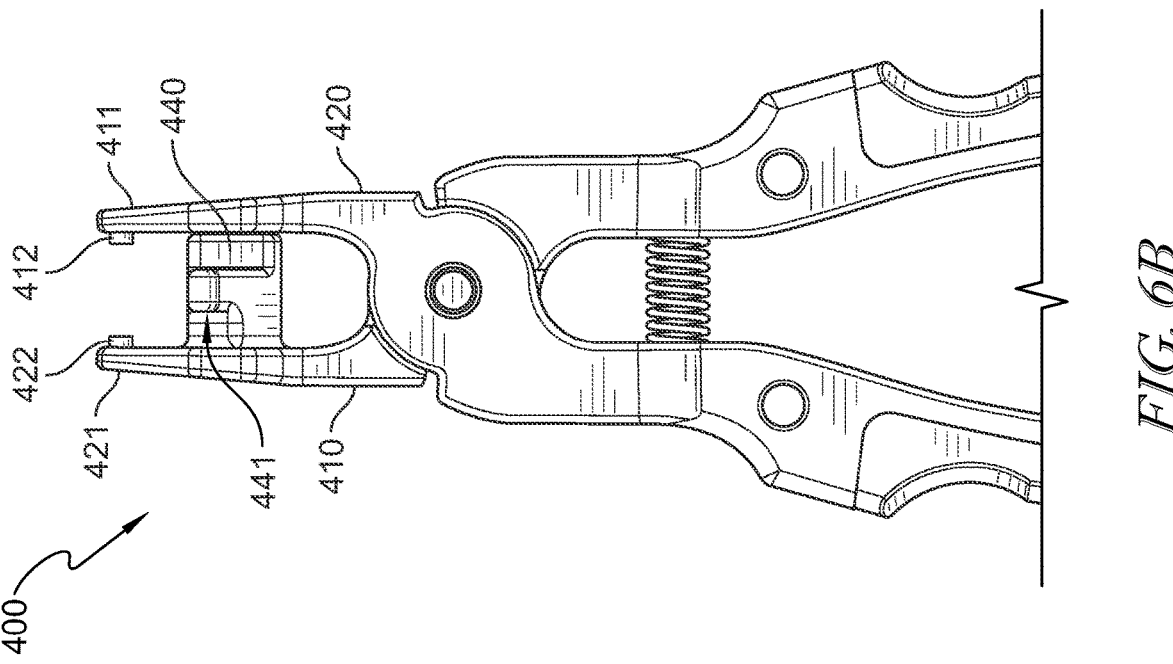
FIG. 6B is a bottom detail view of the distal end of the instrument of FIG. 6A in a closed position.
Figure 6A:
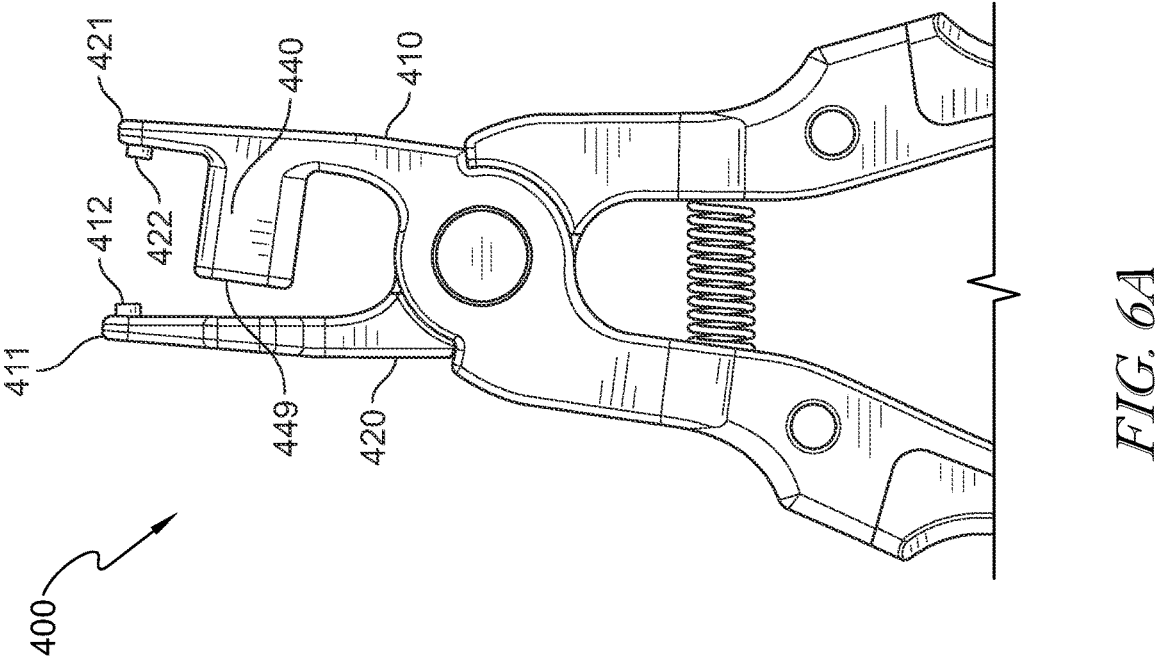
FIG. 6A is a top detail view of the distal end of another example embodiment of a rod rocker reducer instrument in an open position.

The third protrusion 441 can, for example, be used to contact and reduce the rod while rotating the instrument at a smaller angle of rotation. FIG. 6A shows a top view of the jaws 400 in an open position and FIG. 6B is a bottom view of the jaws 400 in a closed position. A first jaw 410 includes a rigid body extending medially toward a second jaw 420. A first protrusion 412 extends medially from the distal end 411 of the first jaw 410 and a second protrusion 422 extends medially from the distal end 412 of the second jaw 420.

Figure 6C:
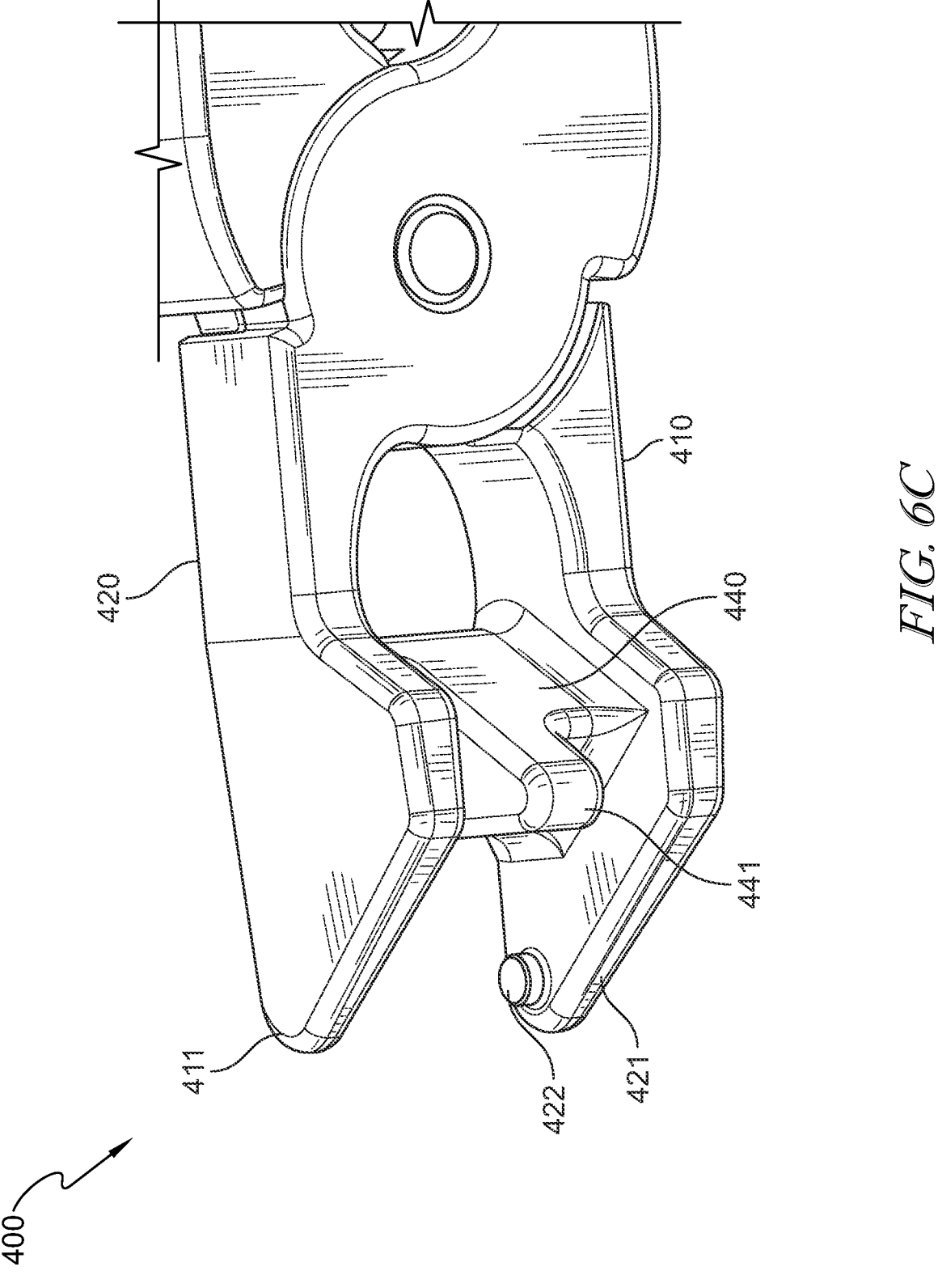
FIG. 6C is an isometric view of the bottom side of the jaws of the instrument of FIG. 6A in the closed position.
Figure 6D:
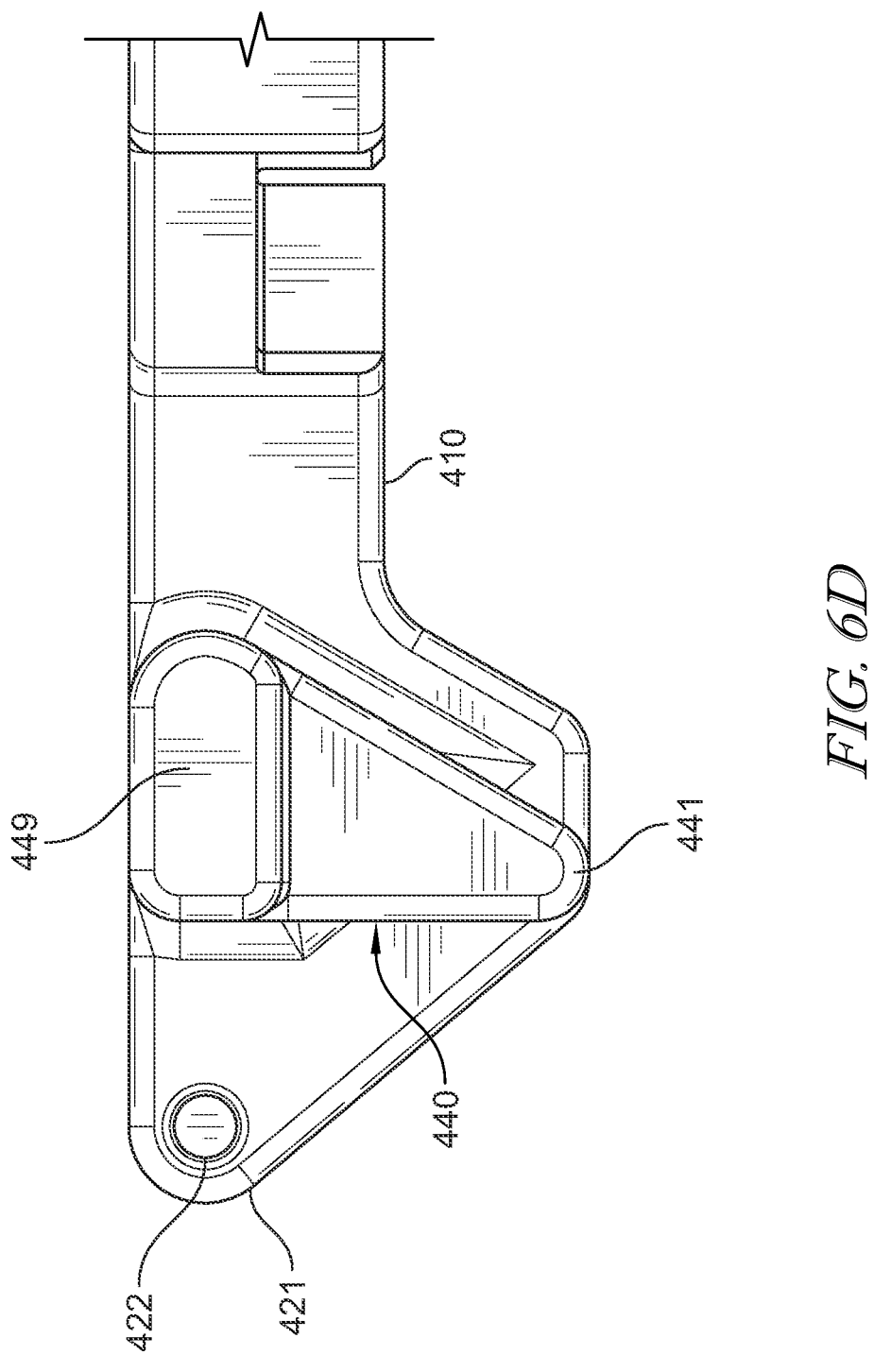
FIG. 6D is a side view of one of the jaws of the instrument of FIG. 6A.

FIG. 6C shows a bottom side view of the jaws 400 in the closed position. In the closed position, the distal ends of the jaws 411, 421 are minimally spaced apart. The third protrusion 441 extends downward from the rigid body 440 to make contact with a spinal rod that can be aligned between the jaws 400. The terminal end of the rigid body 449 is shown from the side in FIG. 6D. The first and second jaws 410, 420 are configured to move together when the instrument is moved from an open position to a closed position. In the present embodiment, the stop arrangement is defined by an abutment between the rigid body 440 and the second jaw 420. As the jaws 400 move together, the terminal end 449 of the rigid body 440 makes contact with the second jaw 420 defining the closed position. The contact between the rigid body 440 and second jaw 420 prevents further movement of the jaws 400 and therefore prevents further movement of the first and second protrusions 412, 422. This prevents the jaws 400 from exerting excess clamping force on a receiver. Accordingly, the terminal end 449 and the second jaw 420 define a stop arrangement for the jaws 400.

Pinned Footed Rocker Instrument with Alternate Locking Mechanism

Figure 7B:
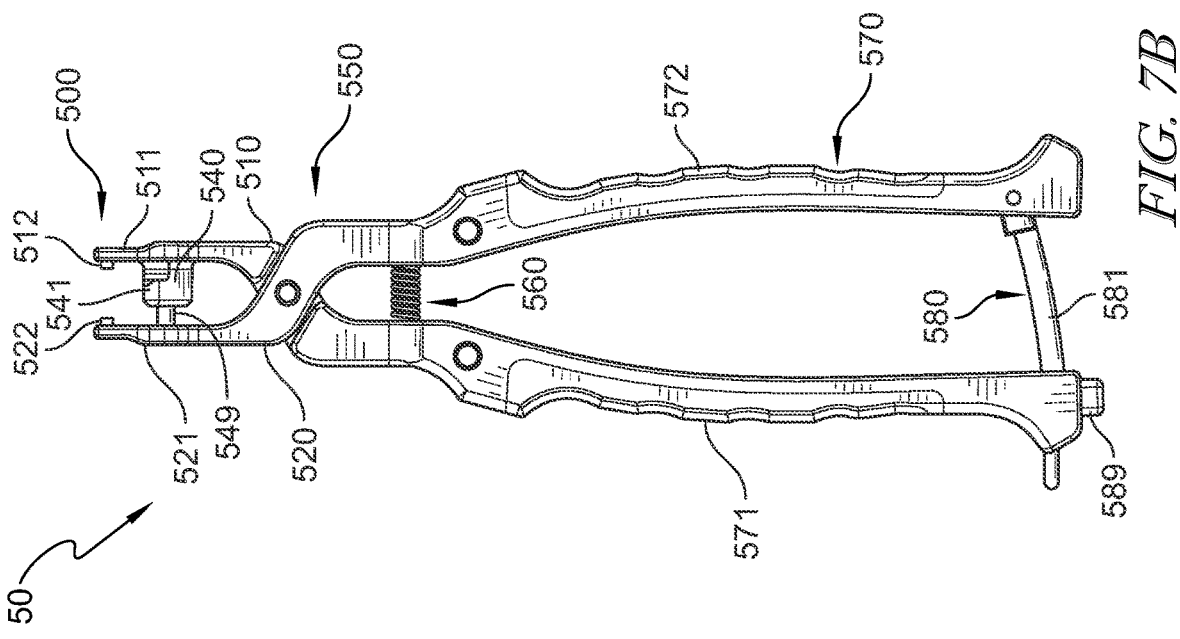
FIG. 7B is a bottom view of the instrument of FIG. 7A in an open position.
Figure 7A:
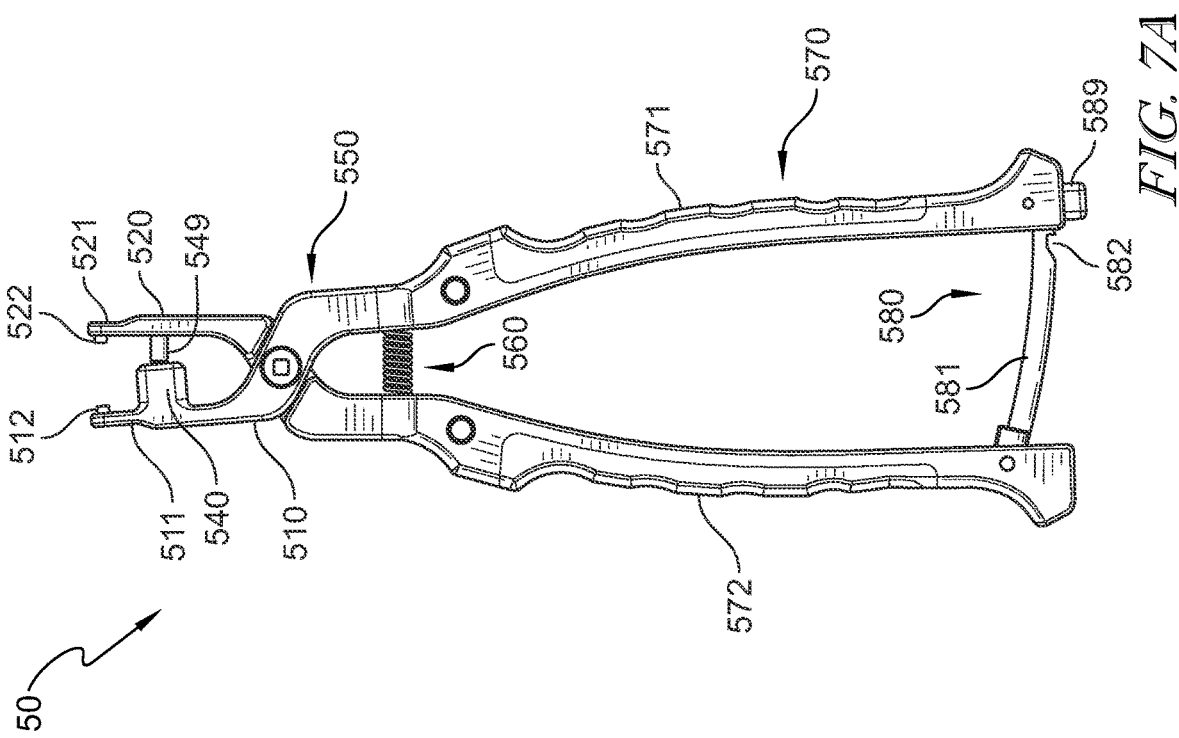
FIG. 7A is a top view of another example embodiment of a rod rocker reducer instrument in an open position.
Figure 7C:
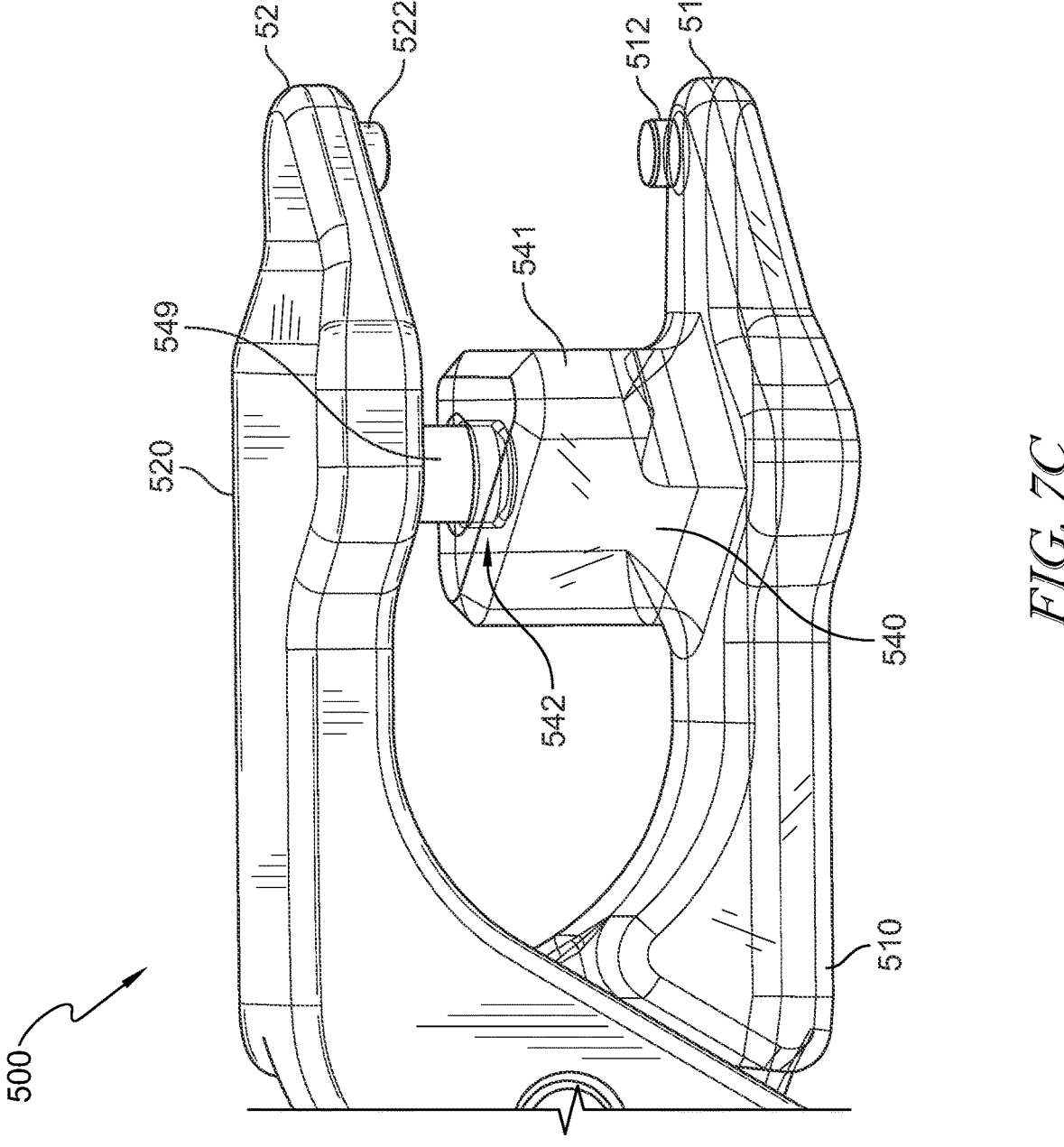
FIG. 7C is an isometric view of the bottom side of the jaws of the instrument of FIG. 7A in the closed position with one of the jaws illustrated as transparent.

FIG. 7A-7C illustrate another example embodiment of a rod rocker reducer instrument. Similar to the embodiment initially presented in FIGS. 1A-3E, the instrument 50 shown in FIGS. 7A and 7B includes a first jaw 520 with a distal end 521 and a second jaw 510 with a distal end 511 that are coupled to a first handle 571 and a second handle 572 by an adjustment mechanism 550. A biasing mechanism 560, such as a spring, can be disposed between the first handle 571 and the second handle 572, proximal to the adjustment mechanism 550. A locking mechanism 580 can be disposed between the proximal ends of the handles 570. As seen in FIG. 7A, the locking mechanism 580 includes a bar 581 extending from the proximal end of the second handle 572 and into the proximal end of the first handle 571 where a notch 582 in the bar 581 is able to be captured by a retention mechanism (not shown—disposed inside the first handle 571) of the locking mechanism 580 that holds the bar 581 via engagement with the notch 582 to prevent opening of the handles 571, 572. The retention mechanism is released via a button 589. FIG. 7B shows the handles 571, 572 in a closed position, with the locking mechanism 580 securing the handles 571, 572 in this position by preventing the handles 571, 572 from being opened without first engaging the button 589 to release the retention mechanism that secures the bar 581. Incorporating the button 589 into the first handle
571 allows the design to be less bulky (e.g., fewer compo-
nents) as compared with the locking mechanism of FIGS.
1-4A. The lock button 589 incorporated into the handle is
not limited to the footed design of FIGS. 7A-7C, and can be
part of any embodiment described herein.

The present embodiment differs from the embodiments
described above in that the stop arrangement is defined by a
mating pin 549 and recess 542 of the rigid body 540. The
mating pin 549 and recess 542 of the rigid body 540 is
shown in more detail in FIG. 7C. The second jaw 520
comprises a pin 549 extending towards the rigid body 540 of
the first jaw 510, and the rigid body defines a recess 542 in
a terminal distal end surface that is configured to receive the
pin 549. The pin 549 is configured to bottom out in the
recess 542 to define the closed position such that the first jaw
510 and second jaw 520 are fixed relative to each other.

Long Pinned Footed Rocker Instrument with Distal End
Stop

Figure 8B:
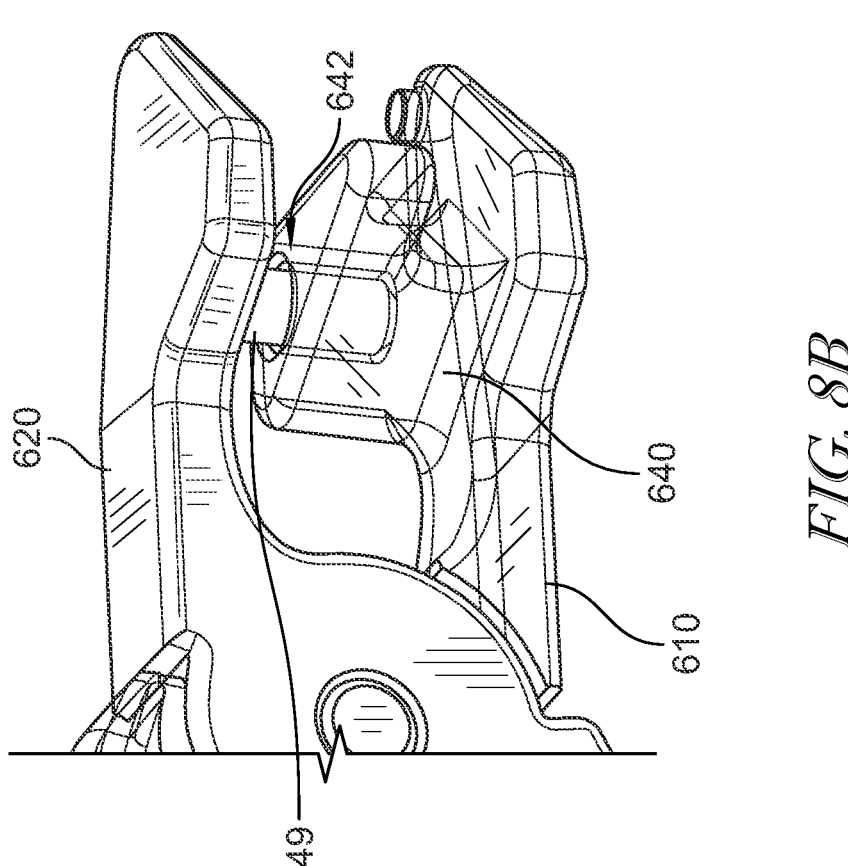
FIG. 8B is an isometric view of the bottom side of the jaws of the instrument of FIG. 8A in a closed position with one of the jaws as transparent.
Figure 8A:
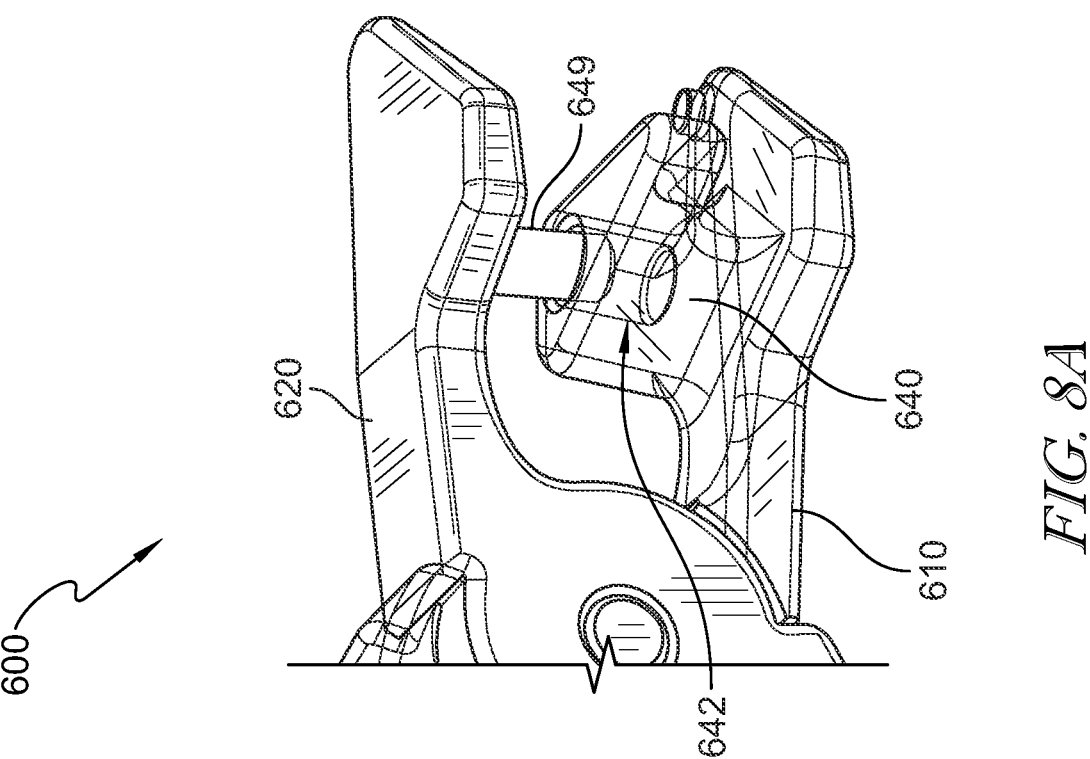
FIG. 8A is an isometric view of the bottom side of the jaws of another example embodiment of a rod rocker reducer instrument in an open position with one of the jaws as transparent.

FIGS. 8A and 8B are isometric views of the bottom side
of first and second jaws 610, 620 of yet another example
embodiment of a rod rocker reducer instrument 600 in an
open position with one of the jaws 610 shown as transparent.
FIG. 8A shows the jaws 610, 620 in an open position and
FIG. 8B shows the jaws 610, 620 of the instrument 600 of
FIG. 8A in a closed position with one of the jaws as
transparent. The instrument embodiments of FIGS. 8A and
8B are variations of the pinned foot instrument 50 embodi-
ment of FIGS. 7A-7C. The primary variation is that the
embodiment of FIGS. 8A and 8B has a pin 649 that mates
with a recess 642 in the foot 640 that is be longer (as
compared with the mating pin 549 and recess 542 of the
rigid body 540 in FIGS. 7A-7C), which is configured to
maintain positive engagement of the jaws with the jaws in
the opening position, as shown in FIG. 8A. In general,
having a longer pin 649 ensures simplicity of alignment of
features and components from a use and a manufacturing
perspective, which can increase reliability. On the other
hand, a shorter pin, such as that of FIGS. 7A-7C, while not
always engaged, can enable wider jaws and therefore
accommodate a higher degree of lateral rod misalignment
with a receiver prior to full engagement of the instrument.

Footed Rocker Instrument with Centralizing Features

Figure 9B:
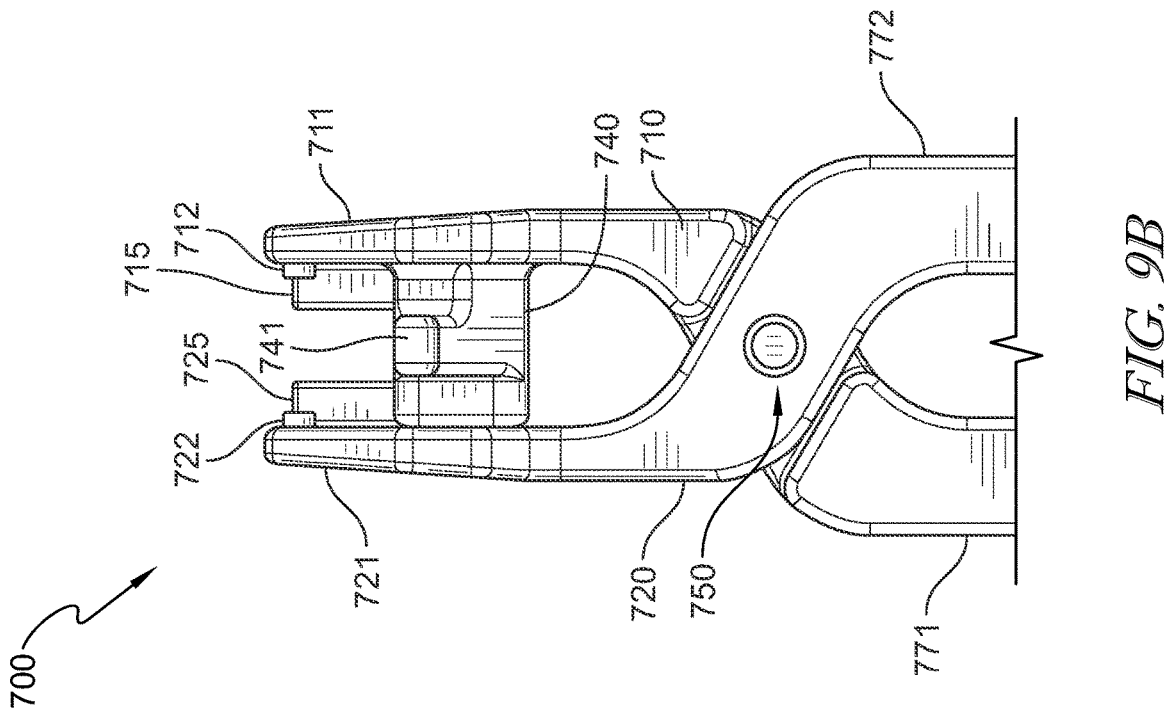
FIG. 9B is a bottom detail view of the jaws and pivot mechanism of the instrument of FIG. 9A in a closed position.
Figure 9A:
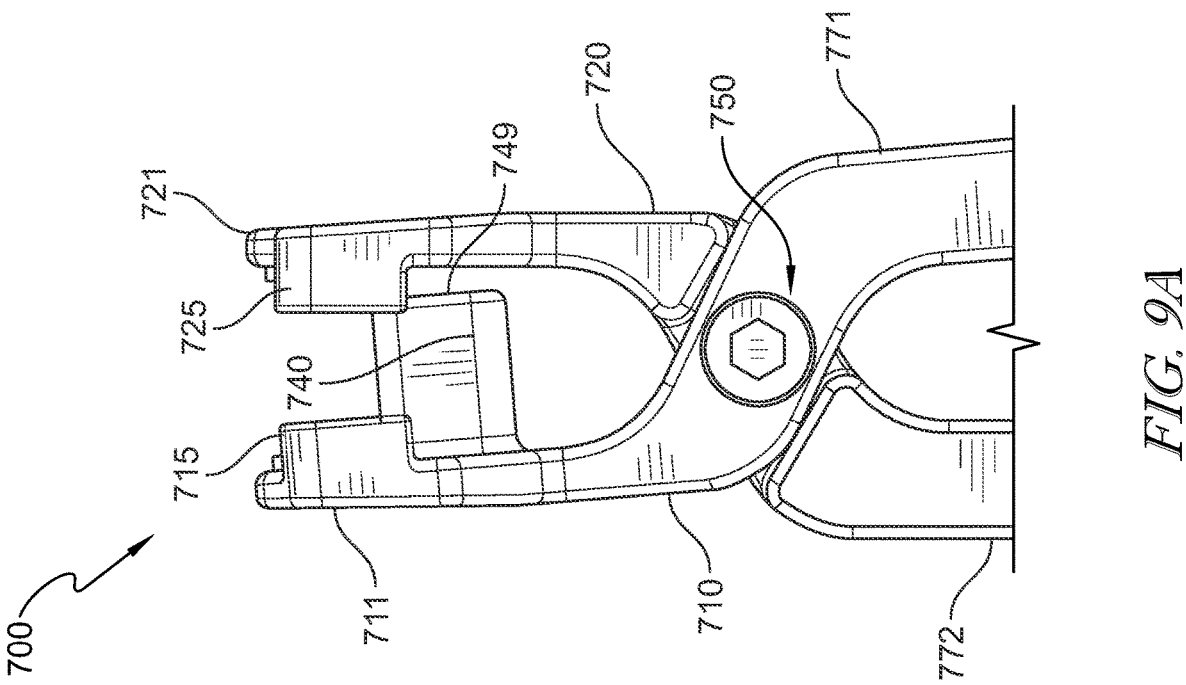
FIG. 9A is a top detail view of the jaws and pivot mechanism of still another example embodiment of a rod rocker reducer instrument in an open position.

Still other alternative embodiments are also contemplated
and provided in the present disclosure. For example, FIGS.
9A-9H illustrate views of one embodiment of jaws 700
wherein the first centralizing feature 715 and second cen-
tralizing feature 725 are positioned at the top side of the first
jaw 710 and second jaw 720 with respect to the first distal
protrusion 712 and second distal protrusion 722. FIG. 9A is
top view which shows the first and second centralizing
features 715, 725 positioned at the top of the jaws 700 and
FIG. 9B is a bottom view which shows the first and second
centralizing features 715, 725.

Figure 9D:
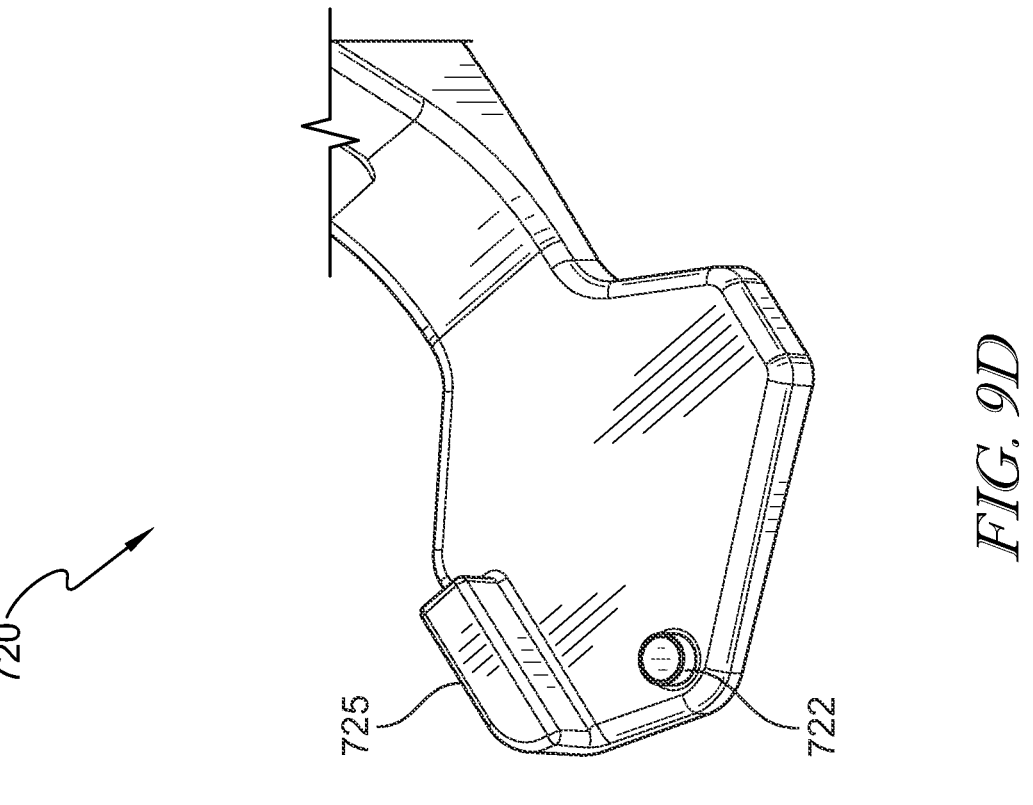
FIG. 9D is an isometric view of a second jaw of the instrument of FIG. 9A.
Figure 9C:
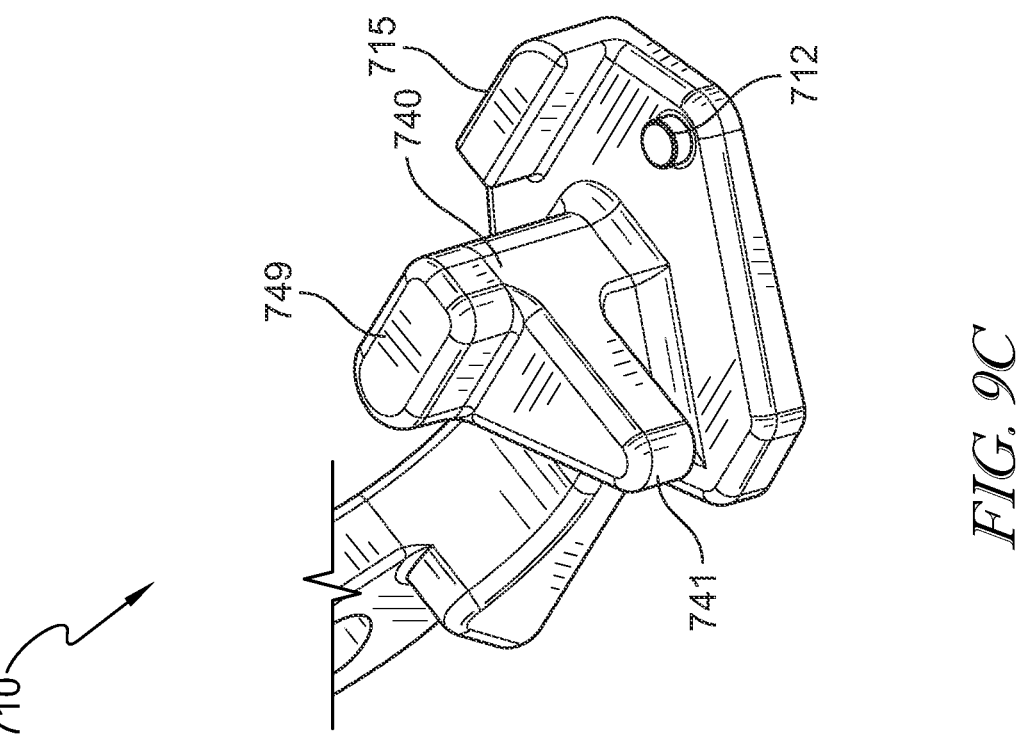
FIG. 9C is an isometric view of a first jaw of the instrument of FIG. 9A.

FIG. 9C illustrates the first jaw 710 in greater detail. A
rigid body 740 extends away from the first jaw 710 and
contains a terminal surface 749, which serves as the stop
arrangement when it contacts the second jaw 720 as the
instrument closes. A third protrusion 741 extends down from
the rigid body and is configured to make contact with a rod
to reduce it into a receiver. The first centralizing feature 715
extends medially from the distal end of first jaw 710 and is
positioned above a distal protrusion 712. FIG. 9D illustrates
the second jaw 720 in greater detail. The second centralizing
feature 725 extends medially from the distal end of the
second jaw 720 and is positioned above a distal protrusion
722.

14

Figure 9F:
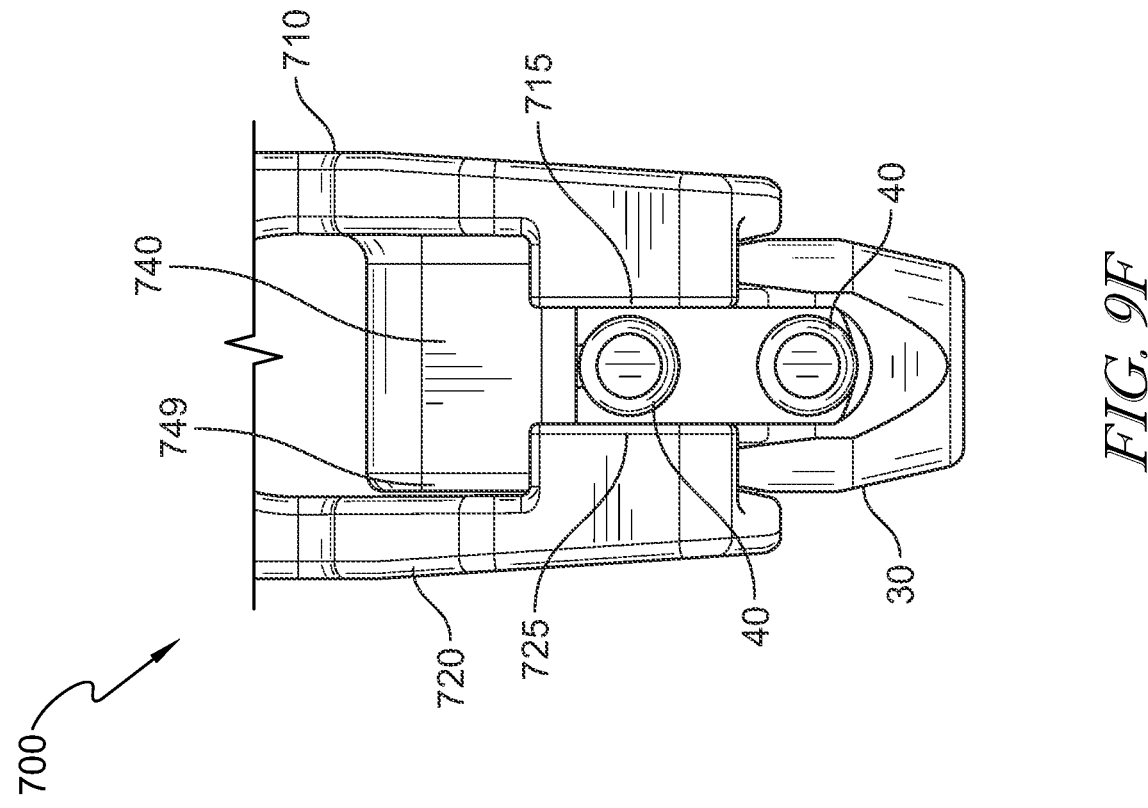
FIG. 9F is front detail view of the jaws of the instrument of FIG. 9A and a receiver with a rod with the jaws coupled to the receiver in a closed position and in an initial position for conducting a rod reduction operation.
Figure 9E:
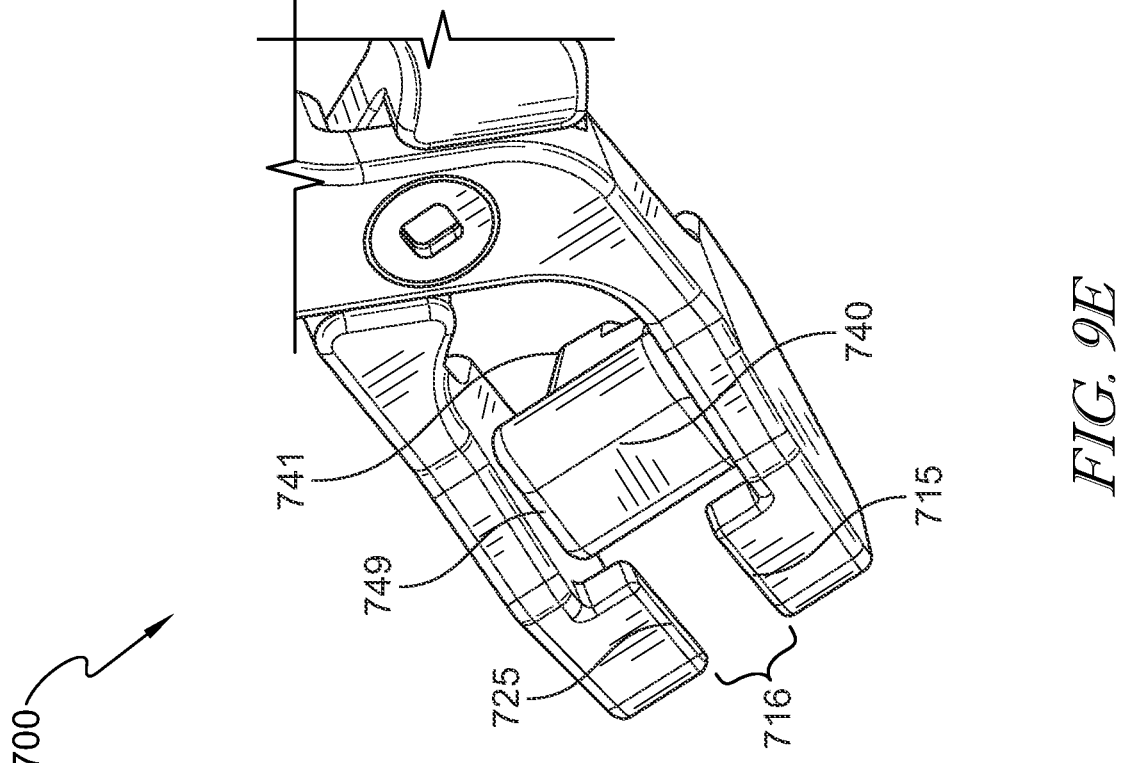
FIG. 9E is an isometric view of the jaws of the instrument of FIG. 9A in the closed position.

FIG. 9E is an isometric view of the jaws of the instrument
of FIG. 9A in the closed position. In the closed position the
first centralizing feature 715 and the second centralizing
feature 725 extend medially along the same axis forming a
channel with a width 716 that can correspond to the width
of the rod-receiving recess in the receiver (or as small as the
rod width) in order to ensure that the rod is disposed along
and above the rod receiving recess of the receiver prior to
reduction into the recess.

FIG. 9F is front detail view of the jaws 700 and a receiver
30 with a rod 40. The jaws 700 are coupled to the receiver
in a closed position and in an initial position for conducting
a rod reduction operation. In the initial position, the first
centralizing feature 715 and second centralizing feature 725
create a channel configured to align with the rod-receiving
recess of the receiver 30. The rod 40 is initially disposed
below the rigid body 740 and between the first centralizing
feature 715 and the second centralizing feature 725. The
rigid body 740 contacts the rod 40 and reduces the rod 40 to
a final position within the receiver.

Figures 9G, 9H:
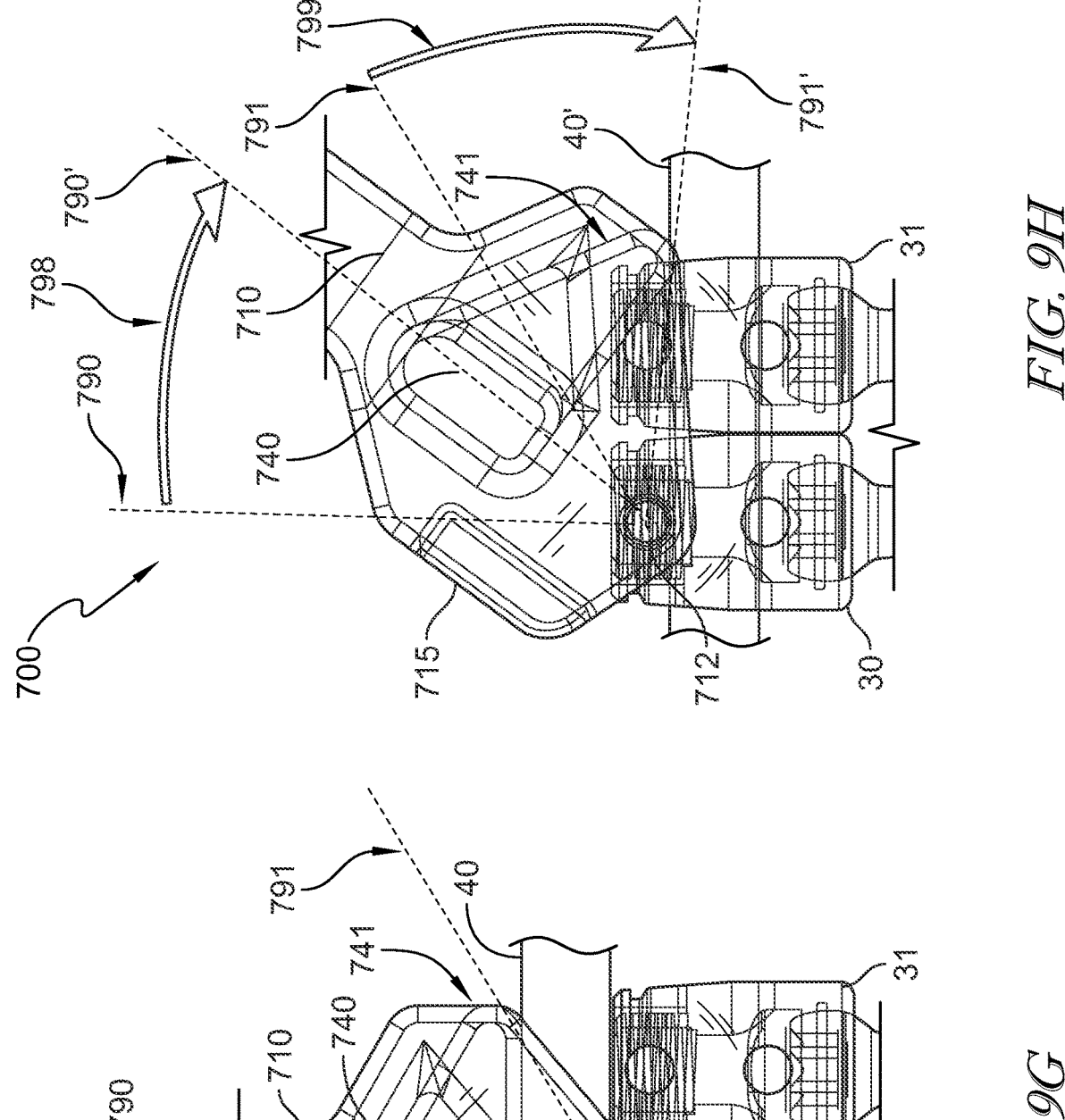
FIG. 9G is a side transparent view of the instrument of FIG. 9A coupled with a receiver and positioned in an initial position with respect to a rod for conducting a rod reduction operation.
FIG. 9H is a side transparent view of the arrangement of FIG. 9G with the instrument moved to a final position after reducing the rod into the receiver.

FIGS. 9G and 9H illustrate side transparent views of the
process of reducing the rod into two receivers using the
footed jaws 700. A distal protrusion 712 is disposed within
a receiver 30 and a rod 40 is aligned above the receiver 30
and below the rigid body 740. In the initial position illus-
trated in FIG. 9G, the rod 40 is disposed between the first
and second centralizing features 715, 725 and the jaws 700
are held in an upright aligning the rigid body 740 with an
initial position 790 of an instrument axis (e.g., from the pivot
location along the jaws) and the distal tip of the third
protrusion 741 contacts the rod 40 along a first position 791
of contact axis (e.g., from the pivot location to the farthest
point of contact between the rod and the third protrusion
741). The first and second centralizing features 715, 725 are
located at the top of the jaws 700 and serve to align the rod
above the rod-receiving recess of the receiver. To reduce the
rod 40 into the receivers 30, 31, a user rotates the jaws 700
of the instrument in a downward direction (as indicated by
arrow 798) which applies force to the rod 40 via the third
protrusion 741 to reduce the rod 40 into the receivers 30, 31
until the third protrusion 741 of the rigid 740 body has
moved the rod 40 into the position 40' of FIG. 9H. In FIG.
9H, the contact axis is rotated to a second position 791' (as
indicated by arrow 799) and the instrument axis is rotated to
a second position 790' (as indicated by arrow 798). The
extension and location of the third protrusion 741 allows for
the jaws 700 to contact the rod to reduce the rod 40 at a point
further from the receiver 30 to which the jaws 700 are
pivotably coupled. Contacting the rod 40 at a point further
from the receiver 30 is advantageous in situations where a
second receiver 31 is placed immediately next to the first
receiver, as illustrated in FIGS. 9G and 9H, and also
decreases the rotation (e.g., 798) of the instrument needed to
reduce the rod. With this embodiment, the user can capture
the first receiver 30 with the jaws 700 and the third protru-
sion 741 will contact the rod 40 to reduce it fully into both
receivers 30, 31. When the jaws 700 rotate to the final
position of FIG. 9H the rod 400 will leave the channel
formed by the first and second centralizing features 715, 725
and enter the rod-receiving portions of the receivers 30, 31.

The footed rocker designs disclosed herein presented a
number of advantages. For example, the shape and size of
the third protrusion 741 can be designed such that the third
protrusion 741 is centrally located above the rod 40 and
allows for an adjacent receiver 31 to be located close to or
immediately next to the receiver 30 that the instrument is
connected to when the instrument fully reduces the rod 40.

For example, FIG. 9H shows receivers 30 and 31 contacting each other, which illustrates that using the instrument is not restricted by the position of the receivers (e.g., the receivers can be as close as possible or farther away from each other and the instrument will still be able to function). Examples presented herein advantageously combine the benefits of the foot (e.g., being able to reduce a rod into two screw heads that are abutting) with a pair of actively closing rocker jaws. Additionally, other benefits of actively locking rocker jaw over a static rocker are generally easier positive engagement and more secure engagement, which also affords more control over the screw head (e.g., medial/lateral manipulation prior to set screw tightening).

Dual Sided Cross Pin Rocker Instrument

Another example of the present disclosure is shown in FIGS. 10A-10F, which illustrate a dual-sided cross pin rocker instrument 800. The instrument 800 includes first and second jaws 810, 820 with distal protrusions 812, 822 (as detailed above), and further includes two separate rigid bodies that extend between the jaws 810, 820 on opposite lateral sides with respect to the distal protrusions 812, 822: a first body 830a configured to reduce a rod when the instrument 800 is rotated about the distal protrusions 812, 822 in a direction towards the first body 830a and a second body 830b configured to reduce a rod when the instrument is rotated is rotated about the distal protrusions 812, 822 towards the second body 830b. The first and second bodies 830a, 830b each have a step 839a, 839b that engages a corresponding opening 829a, 829b in the second jaw 820 to define a stop arrangement of the first and second jaws 810, 820.

Figures 10A, 10B:
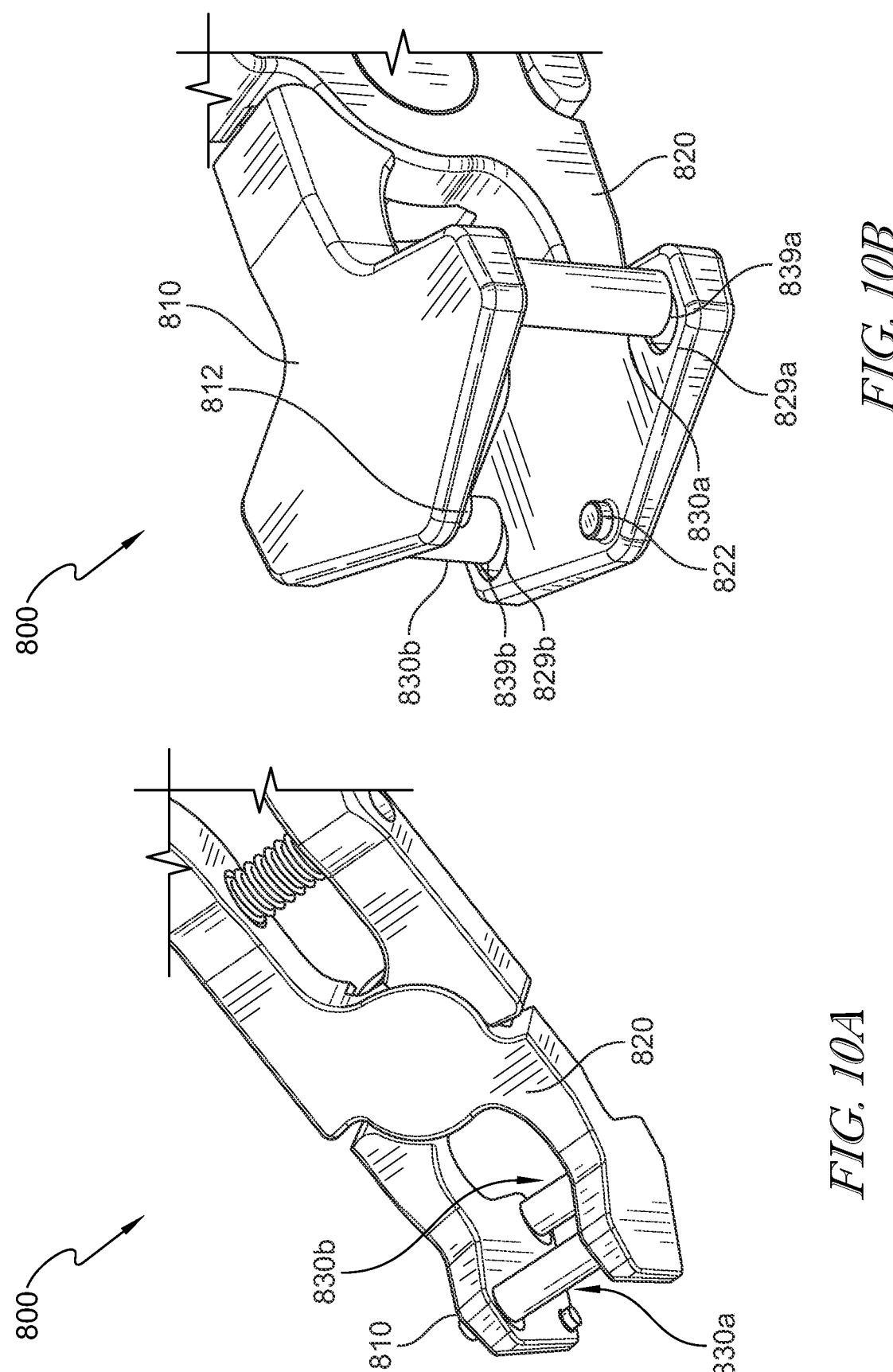
FIGS. 10A and 10B are isometric view of the jaws of another example embodiment of a rod rocker reducer instrument in a closed position.
Figures 10C, 10D:
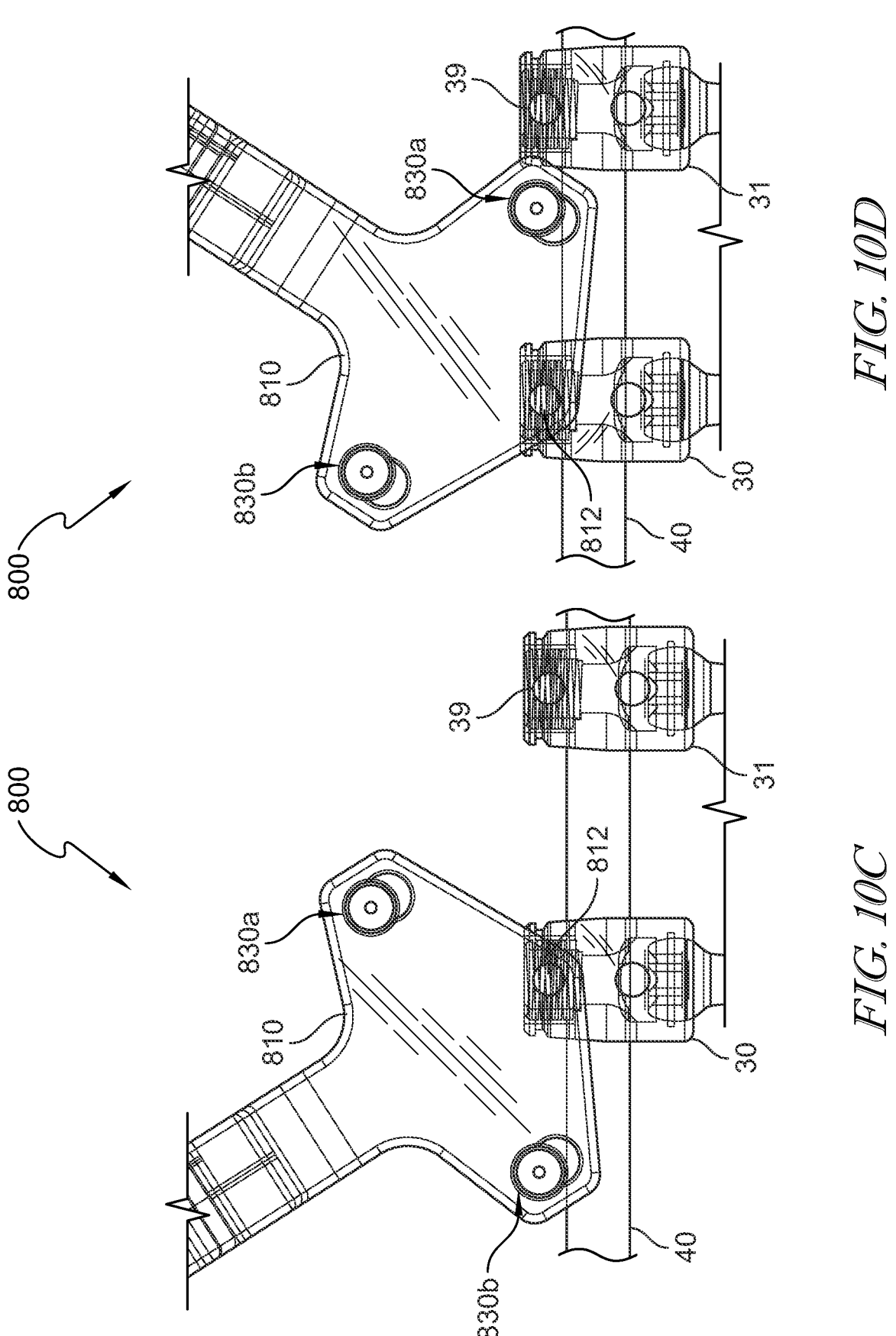
FIG. 10C is a side schematic view of the instrument of FIG. 10A coupled with a receiver and positioned in a final position after reducing the rod into the receiver in a first direction.
FIG. 10D is a side schematic view of the instrument of FIG. 10A coupled with a receiver and positioned in a final position after reducing the rod into the receiver in a second direction.
Figures 10E, 10F:
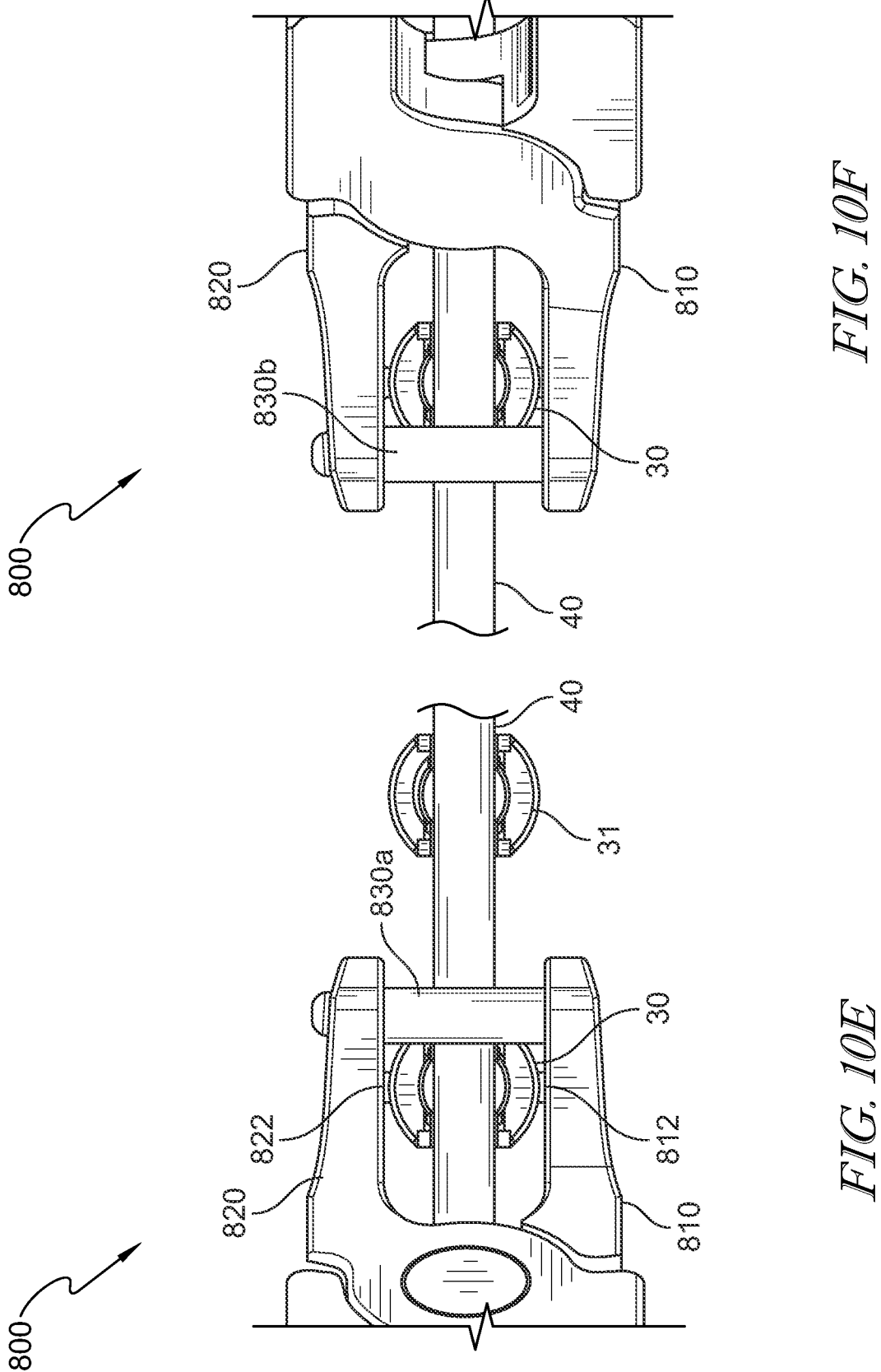
FIG. 10E is a top view of the configuration of FIG. 10C.
FIG. 10F is a top view of the configuration of FIG. 10D.

The dual-sided design of the instrument 800 of FIGS. 10A-10F advantageously enables connection the instrument 800 to a receiver implant once and without needing to remove the instrument 800 to apply a reduction force in an opposite direction than originally planned. FIGS. 10C and 10D show the end of a reduction operation of a rod 40 into a receiver in two different directions and FIGS. 10E and 10F, respectively, show a top-down view of the arrangements of FIG. 10C or 10D. In FIG. 10C, the instrument 800 was rotated counterclockwise about the recesses 39 in the receiver 30 and in FIG. 10D, the instrument was rotated clockwise. Both the counterclockwise and clockwise rotations of the instrument 800 are possible once the instrument 800 is coupled (e.g., closed) with the receiver 30 and without decoupling (e.g., opening) the jaws 810, 820. The instrument 800 can be symmetric along its central plane (e.g., distal geometries and cross pin 830a, 830b locations are mirrored, and the distal protrusions 812, 822 to connect with the receiver 30 are located along the central plane). However, a dual-sided rocker instrument does not have to be symmetric and examples include asymmetric arrangements that can, for example, achieve a different amount of rod reduction on either side (e.g., in opposite rotation directions). Another alternative example includes one-side lateral side (e.g., first body 830a) having a cross pin configuration and the opposite lateral side (e.g., second body 830b) having a rocker foot design. Another example embodiment includes both the first body 830a and the second body 830b of the jaws 810, 820 having a rocker foot design.

Cross Pin Rocker Instrument with Single-Sided Offset Locking Groove

Figures 11A, 11B:
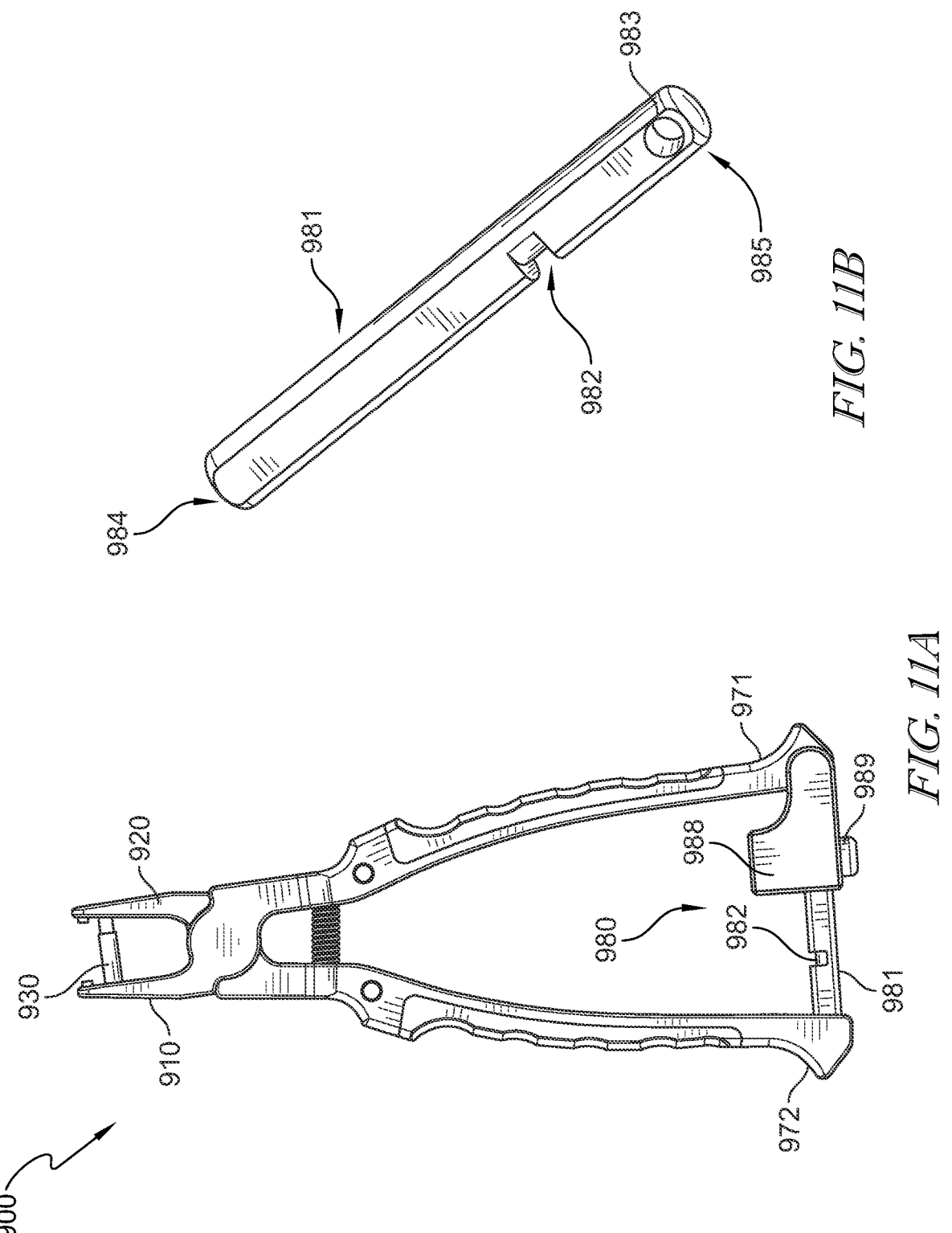
FIG. 11A is a top view of another example embodiment of a rod rocker reducer instrument in an open position with an alternate lock bar design.
FIG. 11B is an isometric view of the lock bar of FIG. 11A.

FIG. 11A is a top view of another example embodiment of a rod rocker reducer instrument in an open position with an alternate lock bar design. The instrument 900 is largely similar to the instrument 10 of FIG. 1 and includes first and second jaws 910, 920 with a cross pin 930, and first and second handles 971, 972 with a locking mechanism 980 connecting the proximal ends of the handles 971, 972. Compared to the instrument 10 of FIG. 1, the instrument 900 includes a locking mechanism 980 that includes a lock bar 981 that has a single-sided off-center locking groove 982 that serves to actuate the locking mechanism. The groove 982 into which the retention mechanism (e.g., activated by the button 989) falls is a one sided groove, instead of fully circumferential (as shown in FIG. 2A). The single-sided off-center locking groove 982 prevents the button 989 housing from falling into the groove on the proximal side (which can causing a false indication of locking). FIG. 11B is a detail view of the lock bar 981, which includes a first end 985 that includes an opening 983 for coupling with the proximal end of the second handle 972 and a second end 984 that slidably extends into the housing 988 of the locking mechanism 980.

Cross Pin Rocker Instrument without Locking Mechanism

Figure 12:
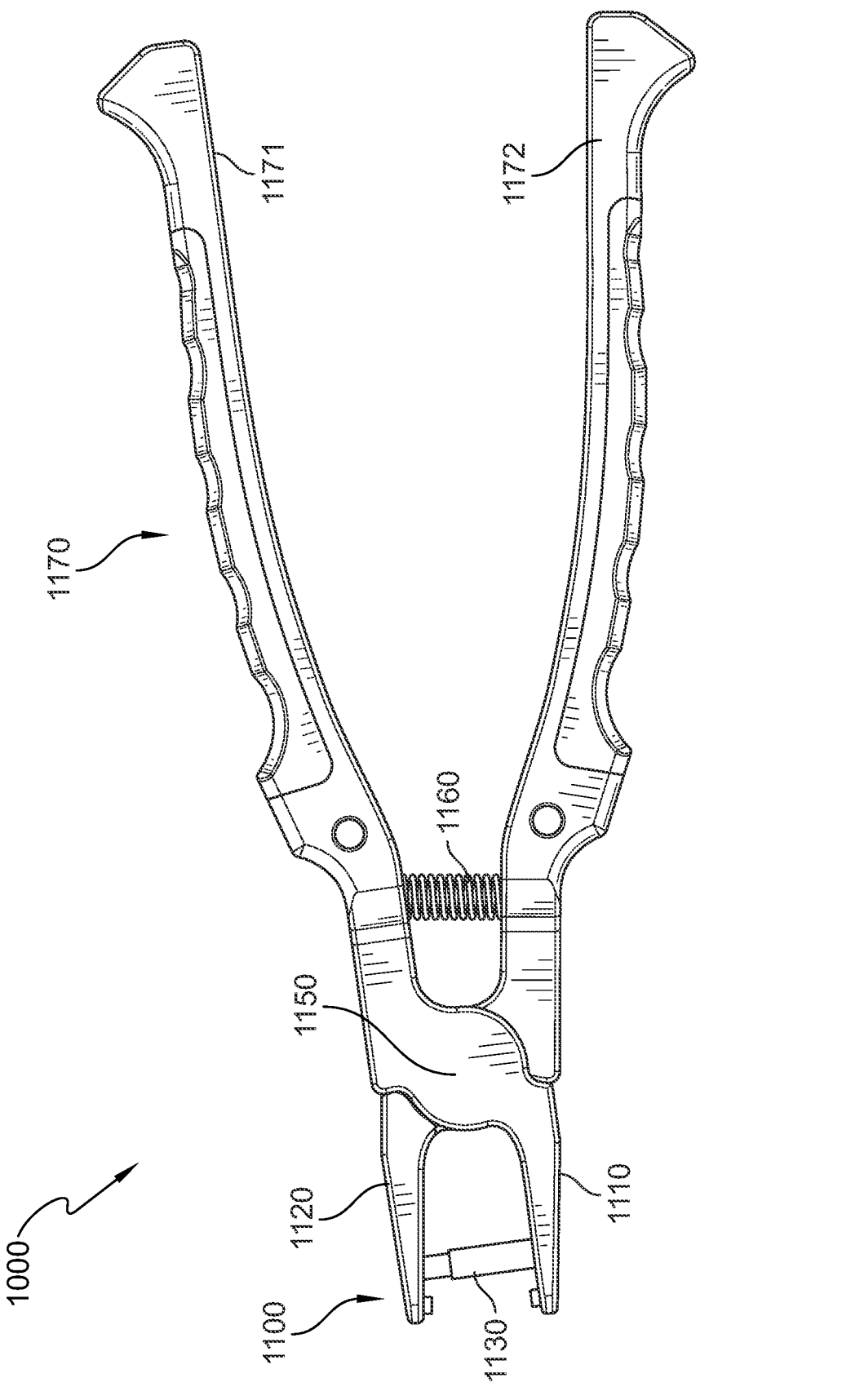
FIG. 12 is a top view of another example embodiment of a rod rocker reducer instrument without a locking mechanism.

FIG. 12 is a top view of another example embodiment of a rod rocker reducer instrument 1000 without a locking mechanism. The instrument 1000 is largely similar to the instrument 10 of FIG. 1 and includes first and second jaws 1110, 1120 with a cross pin 1130, and first and second handles 1171, 1172 but without a locking mechanism connecting the handles 1171, 1172. Compared to the instrument 10 of FIG. 1, the instrument 1100 is simpler to use in that a user does not have to actuate anything in order to remove the instrument 1000 from the receiver that the instrument 1000 is connected to. Instead, a user can loosen their grip to allow the handles 1171, 1172 to expand open under the bias of the spring 1160 after the rod has been secured into the receiver.

Cross Pin Rocker Instrument with Locking Mechanism

Figures 13A, 13B:
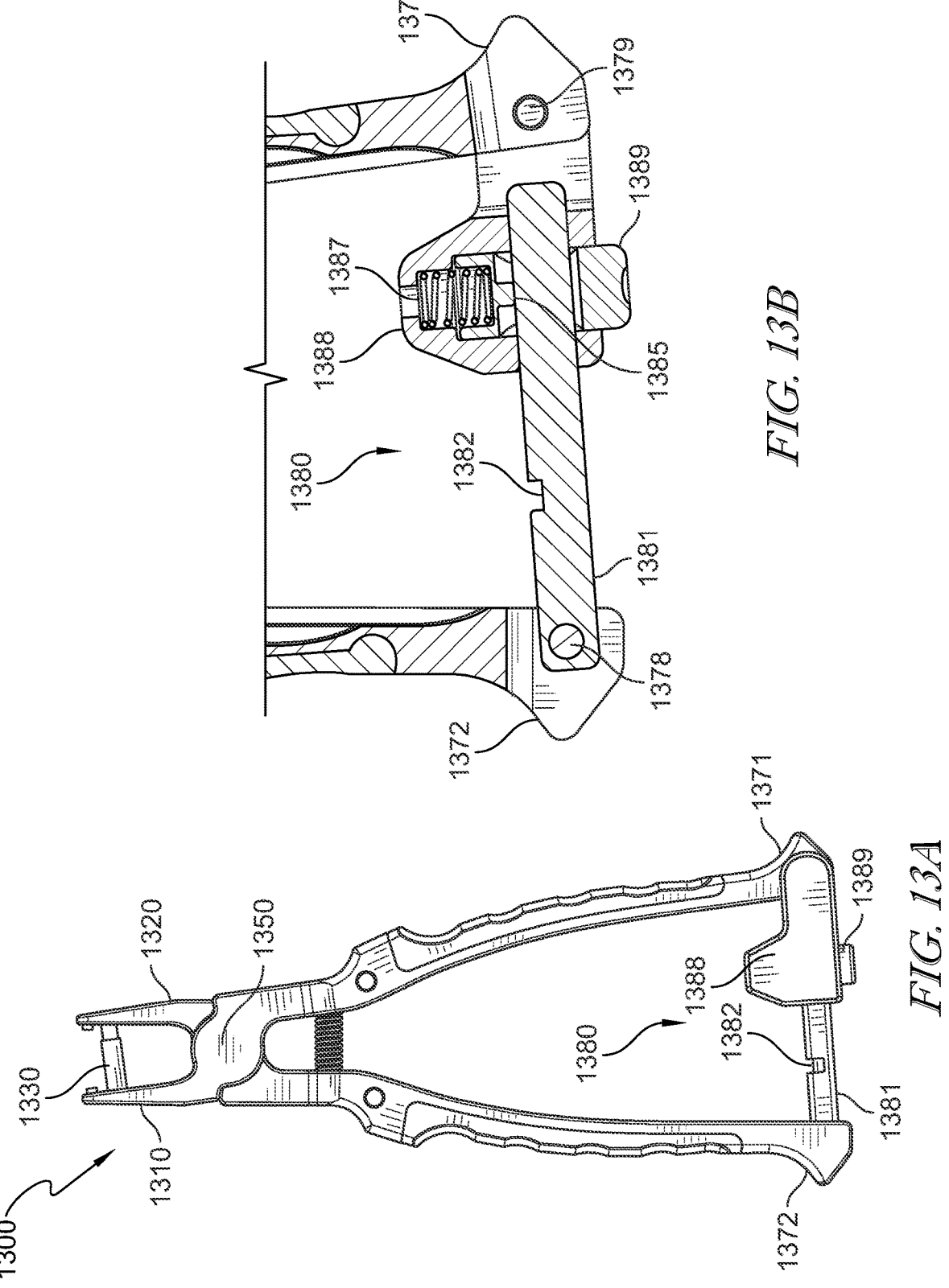
FIG. 13A is a top view of another example embodiment of a rod rocker reducer instrument in an open position with a cross pin and a locking bar locking mechanism.
FIG. 13B is a cross-sectional view of the locking mechanism of the instrument of FIG. 13A in an open and unlocked configuration.
Figures 13C, 13D:
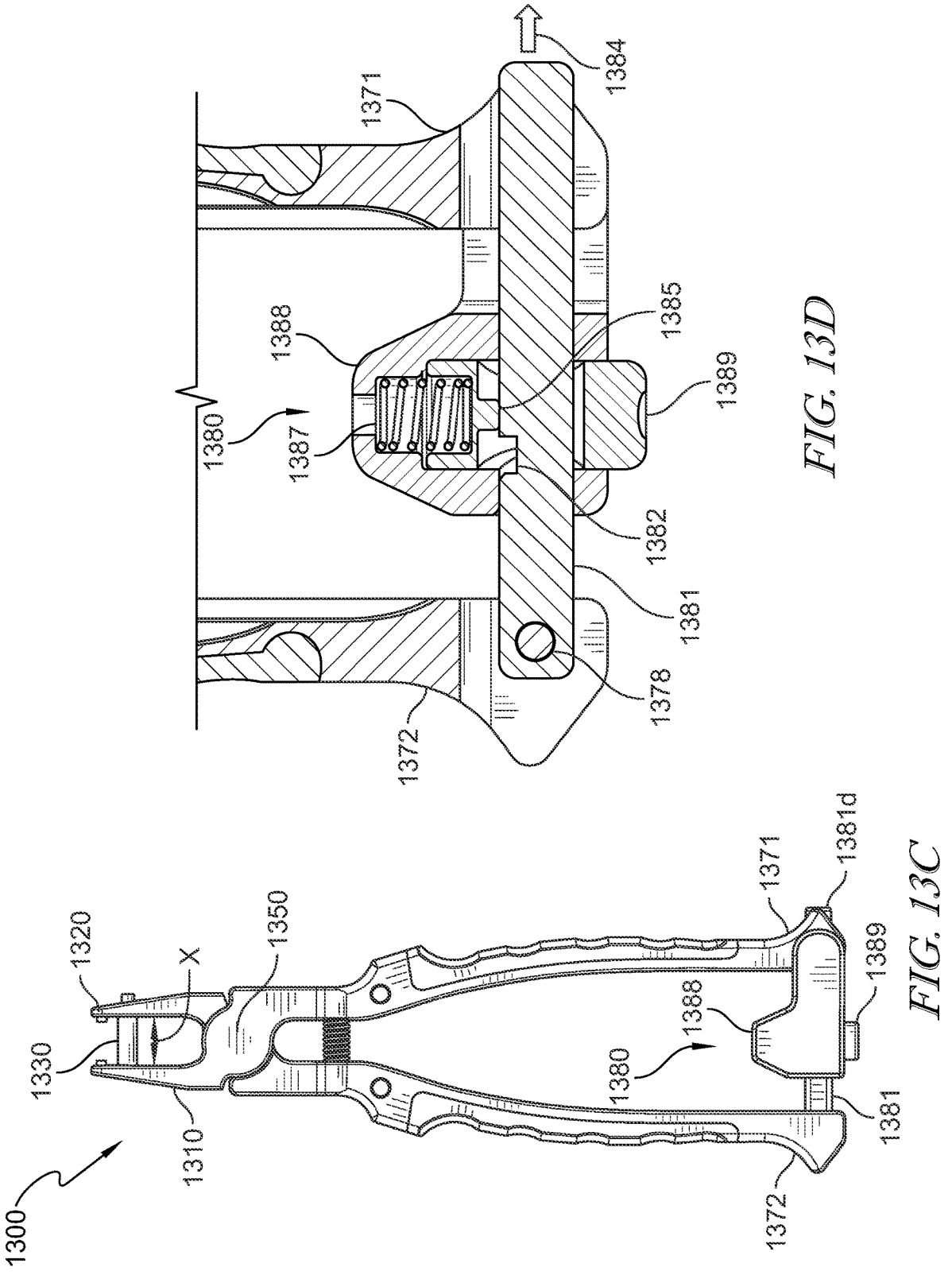
FIG. 13C is a top view of the instrument of FIG. 13A in a closed position with the locking mechanism unlocked.
FIG. 13D is a cross-sectional view of the locking mechanism of the instrument of FIG. 13C in a closed and unlocked configuration.

FIG. 13A is a top view of yet another example embodiment of a rod rocker reducer instrument 1300 in an open position. The instrument 1300 includes a locking mechanism 1380 that includes a locking bar 1381 extending from a pivoting connection to a proximal end of a second handle 1372 into a housing 1388 of the locking mechanism that is pivotably connected to a proximal end of a first handle 1371. The distal end of the instrument 1300 includes an adjustment mechanism 1350 that pivotably connects the first and second handles 1371, 1372 and enables opening and closing of first and second jaws 1310, 1320 that include a cross pin 1330 disposed therebetween with a similar configuration to the pin arrangement of FIGS. 2A-2F, 5A-5D, and 11A. A closed position of the jaws 1310, 1320 (as shown in FIG. 13C) is defined by the cross pin 1330 into the second jaw 1320 up to a point where no further insertion is possible due to the shape of the cross pin 1330. In the open position of FIG. 13A, the jaws 1310, 1320 are fully open, with no further spreading possible due to, for example, the arrangement of the adjustment mechanism 1350 limiting further opening movement. In this open position, the locking mechanism 1380 permits squeezing of the handles 1371, 1372 to close the jaws, which moves the locking bar 1381 into the housing 1388. FIG. 13B is a cross-section of the locking mechanism 380 and shows the pivoting connection 1378 of the locking bar 1381 with the proximal end of the second handle 1372 as well as the pivoting connection 1379 of the housing 1388 with the proximal end of the first handle 1371. The cooperation of these two pivots 1378, 1379 allows the housing 1388 to slidably receive the locking back 1381 in any position of the handles 1371, 1372 without binding. The housing 1388 of the locking mechanism 1380 includes a moveable button 1389 that includes a protrusion 1385 that is biased by a spring 1387 within the housing 1388 to be urged proximally against the locking bar 1381. In operation, a user closing the handles 1371, 1372 also moves the locking bar 1381 further into the housing 1388, which brings a distal-facing groove 1382 closer to the protrusion 1385. Once a user has fully closed the handles 1371, 1372, as defined by the position of the cross pin 1330 within the second jaw 1320, the closed position of the first and second jaws 1310, 1320 is defined, as shown in FIG. 13C.

In FIG. 13C, with the jaws 1310, 1320 and handles 1371, 1372 closed, the jaws 1310, 1320 define a fixed width between them (as indicated by distance X of FIG. 13C). The locking bar 1381 is further disposed within the housing 1388 of the locking mechanism, as shown in FIG. 13D (with moveable of the locking bar 1381 indicated by arrow 1384), but the distal-facing groove 1382 of the locking bar 1381 is not engaged with the proximal-facing and proximally-biased protrusion 1385 of the moveable button 1389. Accordingly, while the instrument jaws 1310, 1320 are in a fixed and closed position, opening of the jaws 1310, 1320 by spreading the handles 1371, 1372 is still possible; the instrument 1300 is still in an unlocked configuration, just as when the instrument 1300 is in the open position. Locking the instrument 1300 in the closed position incudes further squeezing of the handles together, as indicated by arrows 1379 of FIG. 13E.

Figures 13E, 13F:
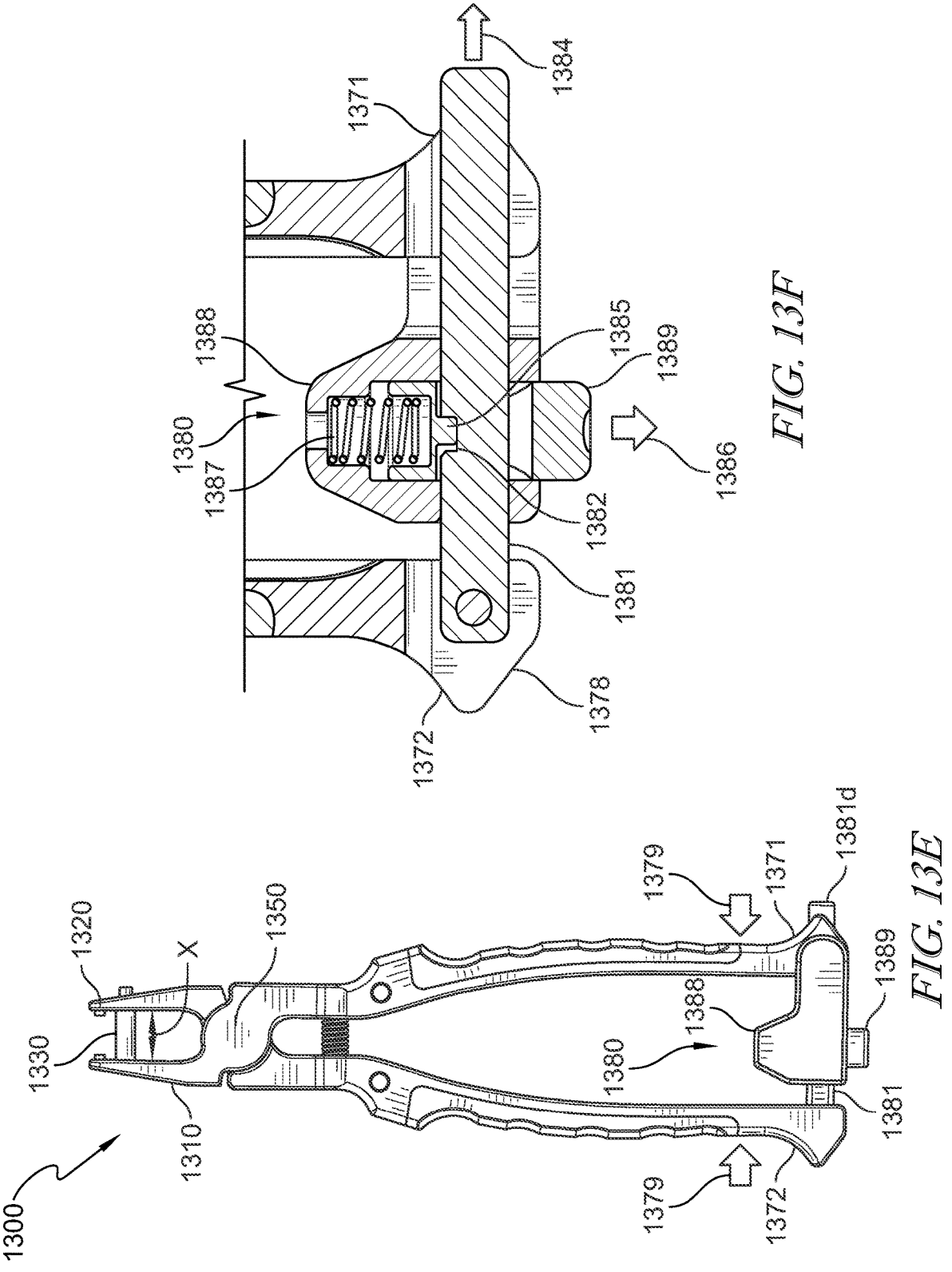
FIG. 13E is a top view of the instrument of FIG. 13A in a closed position with the locking mechanism unlocked.
FIG. 13F is a cross-sectional view of the locking mechanism of the instrument of FIG. 13E in a closed and locked configuration.

In FIG. 13E, a squeezing force applied to the handles 1371, 1372 deflects the handles 1371, 1372 and brings their proximal ends close together without changing the position of the jaws 1310, 1320 (as indicated by the unchanged distance X between them). The deflection of the handles 1371, 1372 further moves the locking bar 1381 into the housing 1388 (as indicated by arrow 1384) until sufficient deflection of the handles 1371, 1372 moves the groove 1382 past the biased protrusion 1385 of the button 1389, at which point the spring 1387 moves the button 1389 proximally (as indicated by arrow 186) and disposes the protrusion 1385 in the groove 1382, as shown in FIG. 13F, thereby transitioning the locking assembly 1380 into a locked configuration. In the locked configuration, the presence of the protrusion 1385 within the groove 1382, as well as the geometric interaction between the groove 1382 and the protrusion 1385, prevents the bar 1381 from being withdrawn from the housing 1388. A user can relax their squeezing of the handles 1371, 1372 without the handles 1371, 1372 moving further apart. Functionally, in the locked configuration, the movement of the bar 1381 is sufficiently constrained by the housing 1388 such that the protrusion cannot dislodge from the groove 1382 and the abutting surfaces of the protrusion and groove are shaped to prevent the forces on the bar from the handles 1371, 1372 from moving the protrusion 1385 proximally. Thus, the locked configuration of the locking mechanism 1380 holds the instrument 1300 in the closed position and maintains tension in the handles 1371, 1372 that hold the jaws 1310, 1320 in the closed position and reduces or eliminates any slack movement of the jaws 1310, 1320, such that the distance between the jaws is strongly maintained during any subsequent manipulation of the instrument 1300 in the closed and locked position.

The instrument 1300, in the locked configuration, can be unlocked by depressing the button 1389 against the force of the bias spring 1387, which moves the protrusion out of the groove 1382 and thereby allows the locking bar 1381 to slide with respect to the housing 1388. When the button 1389 is depressed in the locked configuration, with no squeezing of the handles 1371, 1372, the release of the protrusion 1385 from the groove 1382 allows the deflection of the handles 1371, 1372 to relax and moves the locking bar 1381 back to the unlocked position (e.g., movement opposite to the arrow

1384), after which the handles 1371, 1372 can be kept in the closed position, opened to open the jaws 1310, 1320, or re-locked by squeezing the handles 1371, 1372 together again (as indicated by arrows 1379) until the protrusion 1385 is again aligned with the groove 1382 and disposed therein under the proximal urging of the bias spring 1387.

In some examples, the instrument 1300 is configured such that a maximally-open position of the handles 1371, 1372 does not permit complete withdrawal of the locking bar 1381 from the housing 1388. Additionally, while the locking mechanism 1380 of FIGS. 13A-13F shows a single button biased in the proximal direction being responsible for actuating the locking mechanism 1380, other configurations are possible, such as a multi-step unlocking that can include, for example, a latch or other safety mechanism that must be operated by a user before unlocking via depression of the button is possible. A number of different securing and/or latching mechanisms are possible with the instruments of the present disclosure to selectively lock and unlock the locking bar within the housing, such that deflection of the handles is maintained in the closed and locked configuration.

The instrument 1300 is functionally similar to the instrument 900 of FIGS. 11A and 11B and the descriptions of instrument 900 presented herein also apply to the instrument 1300 of FIGS. 13A-13F. For example, the groove 1382 of the lock bar 1381 is also a single-sided off-center locking groove that serves to actuate the locking mechanism. The groove 1382 into which the retention mechanism (e.g., activated by the button 1389) falls is a one sided groove, instead of fully circumferential (as shown in FIG. 2A). The single-sided off-center locking groove 1382 prevents the button 1389 housing from falling into any groove on the proximal side (which can causing a false indication of locking).

While the examples illustrated above have included jaws that are pivotably coupled such that they rotate together about a single common axis, other adjustment mechanisms and arrangements are within the scope of this disclosure, such as jaws that are translated laterally to open and close, as well as jaws that have one or more elements that swing laterally into place from a position distal to the primary pivot point and jaw-like implements that can have a stationary side and a moving side that come together to define the closed position. A number of adjustment mechanisms and arrangements exist for controlling the movement of one jaw with respect to another. The examples present herein include a pliers-like arrangement with a single-axis rotation point between two handle and jaw structures, however, multi-point and multi-axis arrangements are conceived, which can be used to, for example, adjust the ratio between movement of the handles and movement of the jaws. Additionally, example embodiments include moveable jaws without handles, such as would be connected to a surgical robot or other device for providing a source of mechanical movement for controlling the opening, closing, and reduction operation of the jaws. While the engagement features (e.g., protrusions) and centralizing features included above are static structures, also included in this disclosure are engagement features and/or centralizing features that move or are otherwise actuated into place during operation (e.g., retracting and extending from the jaws). Additionally, while the examples shown above have the entire jaws pivoting about the coupling location between the jaw and the receiver, other arrangements are possible, such as a stationary/static coupling between the distal end of the jaws and the receiver and an integral rotating element (e.g., bearing) on each jaw that enables the rotation of the proximal portion of the jaws about the stationary coupling with the receiver to conduct the reducing operation.

Additionally, while the distal protrusions illustrated above are simple structures configured to be disposed within a complimentary recess on a receiver, also included in this disclosure are engagement arrangements that can more securely and/or reliably couple with a receiver, such as by using tapered protrusions that self-center in the recess during closing of the jaws. Also, while the distal protrusions illustrated above are shown to extend along a common axis when the instrument in closed, other configurations are conceived, such as a ball and socket arrangement with the distal protrusions being spherical or having rounded or spherical portions that engage with corresponding rounded or spherical recesses to enable the protrusions to individually engage with a recess at a large range of approach angles and then allow polyaxial movement to align the opposite protrusion with the corresponding recess such that, once both protrusions are coupled, rotation of the instrument about the receiver is limited to a single axis.

Additional details about receivers are provided in U.S. Patent Publication No. 2022/0280200, entitled "Multi-Feature Polyaxial Screw," and filed Mar. 2, 2022. The entire contents of this application are incorporated by reference herein.

Various devices and methods disclosed herein can be used in minimally-invasive surgery and/or open surgery. While various devices and methods disclosed herein are generally described in the context of surgery on a human patient, the methods and devices disclosed herein can be used in any of a variety of surgical procedures with any human or animal subject, or in non-surgical procedures.

Various devices disclosed herein can be constructed from any of a variety of known materials. Example materials include those that are suitable for use in surgical applications, including metals such as stainless steel, titanium, nickel, cobalt-chromium, or alloys and combinations thereof, polymers such as PEEK, ceramics, carbon fiber, and so forth. Further, various methods of manufacturing can be utilized, including 3D printing or other additive manufacturing techniques, as well as more conventional manufacturing techniques, including molding, stamping, casting, machining, etc.

Various devices or components disclosed herein can be designed to be disposed of after a single use, or they can be designed to be used multiple times. In either case, however, various devices or components can be reconditioned for reuse after at least one use. Reconditioning can include any combination of the steps of disassembly, followed by cleaning or replacement of particular pieces, and subsequent reassembly. In particular, a device or component can be disassembled, and any number of the particular pieces or parts thereof can be selectively replaced or removed in any combination. Upon cleaning and/or replacement of particular parts, the device or component can be reassembled for subsequent use either at a reconditioning facility, or by a surgical team immediately prior to a surgical procedure. Reconditioning of a device or component can utilize a variety of techniques for disassembly, cleaning/replacement, and reassembly. Use of such techniques, and the resulting reconditioned device or component, are within the scope of the present disclosure.

Various devices or components described herein can be processed before use in a surgical procedure. For example, a new or used device or component can be obtained and, if necessary, cleaned. The device or component can be sterilized. In one sterilization technique, the device or component can be placed in a closed and sealed container, such as a plastic or TYVEK bag. The container and its contents can be placed in a field of radiation that can penetrate the container, such as gamma radiation, x-rays, or high-energy electrons. The radiation can kill bacteria on the device or component and in the container. The sterilized device or component can be stored in the sterile container. The sealed container can keep the device or component sterile until it is opened in the medical facility. Other forms of sterilization are also possible, including beta or other forms of radiation, ethylene oxide, steam, or a liquid bath (e.g., cold soak). Certain forms of sterilization may be better suited to use with different devices or components, or portions thereof, due to the materials utilized, the presence of electrical components, etc.

In this disclosure, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B," "one or more of A and B," and "A and/or B" are each intended to mean "A alone, B alone, or A and B together." A similar interpretation is also intended for lists including three or more items. For example, the phrases "at least one of A, B, and C," "one or more of A, B, and C," and "A, B, and/or C" are each intended to mean "A alone, B alone, C alone, A and B together, A and C together, B and C together, or A and B and C together." In addition, use of the term "based on," is intended to mean, "based at least in part on," such that an un-recited feature or element is also permissible.

Further features and advantages based on the above-described embodiments are possible and within the scope of the present disclosure. Accordingly, the disclosure is not to be limited by what has been particularly shown and described. All publications and references cited herein are expressly incorporated herein by reference in their entirety, except for any definitions, subject matter disclaimers, or disavowals, and except to the extent that the incorporated material is inconsistent with the express disclosure herein, in which case the language in this disclosure controls.

Examples of the above-described embodiments can include the following:

1. A surgical instrument for inserting a rod into a receiver, comprising:

a first jaw having a first distal end with a first distal protrusion extending therefrom;

a second opposing jaw having a second distal end with a second distal protrusion extending therefrom;

an adjustment mechanism coupled with a proximal end of the first jaw and a proximal end of the second jaw and configured to control the relative positions of the first and second jaws; and a stop arrangement for defining a closed position of the first jaw and the second jaw, such that, in the closed position, the distal ends of the first and second jaws are spaced apart such that the first and second jaws do not exert a clamping force on the receiver or are prevented from exerting beyond a non-deflecting clamping force on the receiver, wherein, in the closed position, the first distal protrusion extends towards the second jaw and the second distal protrusion extends towards the first jaw, wherein the first jaw comprises a rigid body disposed proximal to the first distal protrusion, the rigid body extending from the first jaw towards the second jaw in the closed position, wherein the first jaw and the second jaw are connected by the adjustment mechanism such that the first and second jaws are configured to move between an open position and the closed position, wherein, in the open position, the first and second distal protrusions are maximally spaced apart and, wherein, in the closed position, the first and second distal protrusions are minimally spaced apart, and wherein the first and second distal protrusions are arranged to contact a spinal implant on opposing sides when the instrument is in the closed position.

2. The instrument of example 1, wherein, in the closed position, the first distal protrusion and the second distal protrusion extend along a same axis.

3. The instrument of any of examples 1 to 2, wherein the rigid body is configured to contact the rod and reduce it into a rod-receiving recess of the receiver when the first and second jaws are in the closed position with the distal protrusions disposed in corresponding recesses in the receiver and the instrument is rotated about the same axis.

4. The instrument of any of examples 1 to 3, wherein adjustment mechanism comprises a pivot mechanism and wherein the first jaw and the second jaw are pivotally connected by the pivot mechanism such that the first and second jaws are configured to rotate between an open position and the closed position, wherein, in the open position, the first and second distal protrusions are maximally spaced apart and, wherein, in the closed position, the first and second distal protrusions are minimally spaced apart.

5. The instrument of any of examples 1 to 4, comprising a first handle and a second handle each extending from the adjustment mechanism and configured to control movement of the first and second jaws via the adjustment mechanism such that relative movement between the first jaw and the second jaw corresponds to relative movement between the first handle and the second handle.

6. The instrument of example 5, further comprising a locking mechanism configured to selectively lock the first and second jaws in the closed position.

7. The instrument of example 6, wherein the locking mechanism is coupled with the first and second handles.

8. The instrument of example 7, wherein the locking mechanism is coupled with proximal ends of the first and second handle.

9. The instrument of any of examples 6 to 8, when the locking mechanism is configured to remain unlocked when the first and second jaws are in the closed position, until the first and second handles are flexed towards each other in response to a squeezing pressure applied to the first and second handles, the flexing locking the locking mechanism and maintain the handles in a flexed position.

10. The instrument of example 6, wherein the locking mechanism has a release mechanism to configured to selectively release the locking mechanism from a locked configuration.

11. The instrument of any of examples 1 to 10, wherein the rigid body of the first jaw is offset from a proximal-distal axis of the first jaw with respect to the first distal protrusion.

12. The instrument of any of examples 1 to 11, wherein, in the closed position, the rigid body extends into an opening of the second jaw.

13. The instrument of example 12, wherein the opening of the second jaw is configured to enable a length of the rigid body to move freely in the opening when the instrument moves from an open position to a closed position.

14. The instrument of example 13, wherein the rigid body extends from the first jaw to a distal end, and comprises a reduced diameter portion located along a portion of the length of the rigid body disposed in the opening.

15. The instrument of example 14, wherein the stop arrangement comprises a transition region defined by the reduced diameter portion of the rigid body, such that the closed position is defined by the reduced diameter portion extending into the opening and the transition region contacting the second jaw to prevent further closure between the first and second jaws.

16. The instrument of example 15, wherein the rigid body defines a stepped cylindrical shape, the rigid body having a first, larger diameter section and a second, small diameter section, wherein second section is disposed within an opening of the second jaw, wherein the transition region comprises a stepped transition region between the first and second sections of the rigid body, and wherein the stepped transition region along with the opening in the second jaw stop defines the arrangement.

17. The instrument of any of examples 1 to 16, wherein the stop arrangement comprises a first and second surfaces of the adjustment mechanism that are configured to move relative to each other when the instrument is moved from the open position to the close position, and wherein the closed position is defined by an abutment of the first and second surfaces such that further closure of the first and second jaws is prevented by geometric interference between the first and second surfaces.

18. The instrument of example 17, wherein the geometric interface on the adjustment mechanism is configured to define the maximum open position of the instrument.

19. The instrument of any of examples 1 to 18, wherein the rigid body defines an abutment surface at a terminal distal end that is configured to contact the second jaw to define the closed position, the abutment surface and the second jaw defining the stop arrangement.

20. The instrument of any of examples 1 to 19, wherein the second jaw comprises a pin extending towards the rigid body of the first jaw, and wherein the rigid body defines a recess in a terminal distal end surface that is configured to receive the pin and wherein the pin is configured to bottom out in the recess to define the closed position such that the pin and recess define the stop arrangement.

21. The instrument of any of examples 1 to 20, comprising a biasing mechanism configured to bias the instrument towards the open position.

22. The instrument of any of examples 1 to 21, wherein the rigid body has a third protrusion extending away from the same axis in the closed position, the third protrusion configured to contact the rod to reduce the rod into the receiver.

US 12,678,204 B2

23

23. The instrument of any of examples 1 to 22, wherein the distal end of the first jaw further comprises a first centralizing feature and the distal end of the second jaw further comprises a second centralizing feature, wherein the first and second centralizing features are configured to contact the rod as the first and second jaws move from the open position to the closed position and move the rod to a predefined position between the first and second jaws in the closed position, wherein the predefined position is configured to align the rod with a rod-receiving recess of the receiver.

24. The instrument of example 23, wherein the first centralizing feature comprises a first centralizing protrusion extending medially from the first jaw and the second centralizing feature comprises a second centralizing protrusion extending medially from the second jaw.

25. The instrument of any of examples 1 to 24, wherein the first and second jaws define a top side and a bottom side the jaws configured to rotate towards the bottom side to reduce a rod into the receiver, and wherein the first and second centralizing features are located towards the top side with respect to the first and second distal protrusions.

26. The instrument of any of examples 1 to 25, wherein the first and second jaws define a top side and a bottom side the jaws configured to rotate towards the bottom side to reduce a rod into the receiver, and wherein the first and second centralizing features are located towards the bottom side with respect to the first and second distal protrusions.

27. A surgical method for inserting a rod into a receiver, comprising:

positioning a first jaw and a second jaw of an instrument on opposing sides of a receiver of a screw inserted into bone;

aligning the rod such that it is disposed between the first and second jaws and above the receiver;

closing the first and second jaws of the instrument such that a first distal protrusion on the first jaw mates with a corresponding recess on the receiver and a second distal protrusion on the second jaw mates with a corresponding recess on the opposing side of the receiver, the closing restricting subsequent movement of the instrument to rotation about a common axis of the first and second distal protrusions and first and second recesses;

continuing closing the instrument until a stopping mechanism is engaged, engagement of the stopping mechanism preventing a clamping force from being applied to the receiver by the first and second jaws or limiting a clamping force applied by the first and second jaws such that there is little or no deflection of the receiver;

rotating the instrument about the first and second distal protrusions to contact a rigid body extending between the first and second jaws against the rod; and continuing rotating the instrument to move the rigid body and the rod until the rod is reduced into a rod-receiving recess of the receiver.

28. The method of example 27, wherein closing the instrument until a stopping mechanism is engaged further comprises closing the instrument until a portion of the rigid body contacts the second jaw before the first and second jaws exert a clamping force on the receiver, the contact preventing further closure of the first and second jaws.

29. The method of any of examples 27 to 28, wherein closing the instrument further comprises applying pressure to a first handle and a second handle extending from a pivot mechanism disposed between the first and second jaws and the first and second handles such that the first jaw rotates relative to the second jaw towards the second jaws.

30. The method of example 29, comprising applying further pressure on the handles to engage a locking mechanism on the proximal ends of the handle to maintain a fixed position between the handles and therefore the jaws, once engaged, the locking mechanism preventing the handles from moving to open the jaws.

31. The method of example 30, comprising, after engaging the locking mechanism, pressing a release button to move the locking mechanism from a locked to an unlocked position, wherein the first and second handles can move to separate the first and second jaws in the unlocked position.

32. The method of any of examples 27 to 31, wherein closing the first and second jaws of the instrument comprises translating a portion of the rigid body through an opening in the second jaw.

What is claimed is:

1. A surgical instrument for inserting a rod into a receiver, comprising:

a first jaw having a first distal end with a first distal protrusion extending therefrom;

a second opposing jaw having a second distal end with a second distal protrusion extending therefrom;

an adjustment mechanism coupled with a proximal end of the first jaw and a proximal end of the second jaw and configured to control the relative positions of the first and second jaws; and a stop arrangement for defining a closed position of the first jaw and the second jaw, such that, in the closed position, the distal ends of the first and second jaws are spaced apart such that the first and second jaws do not exert a clamping force on the receiver or are prevented from exerting beyond a non-deflecting clamping force on the receiver, wherein the stop arrangement includes a rigid body disposed proximal to the first distal protrusion extending from the first jaw towards the second jaw, wherein, in the closed position, the first distal protrusion extends towards the second jaw, the second distal protrusion extends towards the first jaw, and the rigid body extends into an opening of the second jaw, wherein the first jaw and the second jaw are connected by the adjustment mechanism such that the first and second jaws are configured to move between an open position and the closed position, wherein, in the open position, the first and second distal protrusions are maximally spaced apart and, wherein, in the closed position, the first and second distal protrusions are minimally spaced apart, and wherein the first and second distal protrusions are arranged to contact a spinal implant on opposing sides when the instrument is in the closed position.

2. The instrument of claim 1, wherein, in the closed position, the first distal protrusion and the second distal protrusion extend along a same axis.

3. The instrument of claim 2, wherein the rigid body is configured to contact the rod and reduce it into a rod-receiving recess of the receiver when the first and second jaws are in the closed position with the distal protrusions disposed in corresponding recesses in the receiver and the instrument is rotated about the same axis.

4. The instrument of claim 1, wherein the adjustment mechanism comprises a pivot mechanism and wherein the first jaw and the second jaw are pivotally connected by the pivot mechanism such that the first and second jaws are configured to rotate between the open position and the closed position, wherein, in the open position, the first and second distal protrusions are maximally spaced apart and, wherein, in the closed position, the first and second distal protrusions are minimally spaced apart.

5. The instrument of claim 1, comprising a first handle and a second handle each extending from the adjustment mechanism and configured to control movement of the first and second jaws via the adjustment mechanism such that relative movement between the first jaw and the second jaw corresponds to relative movement between the first handle and the second handle.

6. The instrument of claim 5, further comprising a locking mechanism configured to selectively lock the first and second jaws in the closed position.

7. The instrument of claim 6, wherein the locking mechanism is coupled with the first and second handles.

8. The instrument of claim 7, wherein the locking mechanism is coupled with proximal ends of the first and second handles.

9. The instrument of claim 6, wherein the locking mechanism is configured to remain unlocked when the first and second jaws are in the closed position, until the first and second handles are flexed towards each other in response to a squeezing pressure applied to the first and second handles, the flexing locking the locking mechanism and maintaining the handles in a flexed position.

10. The instrument of claim 6, wherein the locking mechanism has a release mechanism configured to selectively release the locking mechanism from a locked configuration.

11. The instrument of claim 1, wherein the rigid body of the first jaw is offset from a proximal-distal axis of the first jaw with respect to the first distal protrusion.

12. The instrument of claim 1, wherein the opening of the second jaw is configured to enable a length of the rigid body to move freely in the opening when the instrument moves from an open position to a closed position.

13. The instrument of claim 12, wherein the rigid body extends from the first jaw to a distal end, and comprises a reduced diameter portion located along a portion of the length of the rigid body disposed in the opening.

14. The instrument of claim 13, wherein the stop arrangement comprises a transition region defined by the reduced diameter portion of the rigid body, such that the closed position is defined by the reduced diameter portion extending into the opening and the transition region contacting the second jaw to prevent further closure between the first and second jaws.

15. The instrument of claim 14, wherein the rigid body defines a stepped cylindrical shape, the rigid body having a first, larger diameter section and a second, small diameter section, wherein the second section is disposed within the opening of the second jaw, wherein the transition region comprises a stepped transition region between the first and second sections of the rigid body, and wherein the stepped transition region along with the opening in the second jaw defines the stop arrangement.

16. The instrument of claim 1, comprising a biasing mechanism configured to bias the instrument towards the open position.

17. The instrument of claim 1, wherein the distal end of the first jaw further comprises a first centralizing feature and the distal end of the second jaw further comprises a second centralizing feature, wherein the first and second centralizing features are configured to contact the rod as the first and second jaws move from the open position to the closed position and move the rod to a predefined position between the first and second jaws in the closed position, wherein the predefined position is configured to align the rod with a rod-receiving recess of the receiver.

18. The instrument of claim 17, wherein the first centralizing feature comprises a first centralizing protrusion extending medially from the first jaw and the second centralizing feature comprises a second centralizing protrusion extending medially from the second jaw.

19. The instrument of claim 17, wherein the first and second jaws define a top side and a bottom side and the jaws are configured to rotate towards the bottom side to reduce a rod into the receiver, and wherein the first and second centralizing features are located towards the bottom side with respect to the first and second distal protrusions.

20. A surgical instrument for inserting a rod into a receiver, comprising:
a first jaw having a first distal end with a first distal protrusion extending therefrom;
a second opposing jaw having a second distal end with a second distal protrusion extending therefrom;
an adjustment mechanism coupled with a proximal end of the first jaw and a proximal end of the second jaw and configured to control the relative positions of the first and second jaws;
a first handle and a second handle each extending from the adjustment mechanism and configured to control movement of the first and second jaws via the adjustment mechanism such that relative movement between the first jaw and the second jaw corresponds to relative movement between the first handle and the second handle;
a stop arrangement for defining a closed position of the first jaw and the second jaw, such that, in the closed position, the distal ends of the first and second jaws are spaced apart such that the first and second jaws do not exert a clamping force on the receiver or are prevented from exerting beyond a non-deflecting clamping force on the receiver; and
a locking mechanism configured to selectively lock the first and second jaws in the closed position, wherein the locking mechanism is configured to remain unlocked when the first and second jaws are in the closed position, until the first and second handles are flexed towards each other in response to a squeezing pressure applied to the first and second handles, the flexing locking the locking mechanism and maintaining the handles in a flexed position;
wherein, in the closed position, the first distal protrusion extends towards the second jaw and the second distal protrusion extends towards the first jaw,
wherein the first jaw comprises a rigid body disposed proximal to the first distal protrusion, the rigid body extending from the first jaw towards the second jaw in the closed position, wherein the first jaw and the second jaw are connected by the adjustment mechanism such that the first and second jaws are configured to move between an open position and the closed position, wherein, in the open position, the first and second distal protrusions are maximally spaced apart and, wherein, in the closed position, the first and second distal protrusions are minimally spaced apart, and wherein the first and second distal protrusions are arranged to contact a spinal implant on opposing sides when the instrument is in the closed position.

21. The instrument of claim 20, wherein, in the closed position, the first distal protrusion and the second distal protrusion extend along a same axis.

22. The instrument of claim 21, wherein the rigid body is configured to contact the rod and reduce it into a rod-receiving recess of the receiver when the first and second jaws are in the closed position with the distal protrusions disposed in corresponding recesses in the receiver and the instrument is rotated about the same axis.

23. The instrument of claim 20, wherein the locking mechanism has a release mechanism configured to selectively release the locking mechanism from a locked configuration.

24. The instrument of claim 20, wherein the locking mechanism is coupled with the first and second handles.

* * * * *